United States Patent
Yamazaki et al.

(10) Patent No.: US 10,253,072 B2
(45) Date of Patent: Apr. 9, 2019

(54) PROPHYLACTIC VACCINE AGAINST EGG DROP SYNDROME (EDS)

(71) Applicant: KM Biologics Co., Ltd., Kumamoto-shi (JP)

(72) Inventors: Kenichi Yamazaki, Kumamoto (JP); Kiyohiko Andoh, Kumamoto (JP); Ryuichi Sakamoto, Kumamoto (JP); Kiyotaka Suenaga, Kumamoto (JP); Takeshi Arakawa, Okinawa (JP); Hirotaka Uefuji, Okinawa (JP); Tetsuya Harakuni, Okinawa (JP); Takeshi Miyata, Kagoshima (JP)

(73) Assignee: KM Biologics Co., Ltd., Kumamoto-shi (JP)

( * ) Notice: Subject to any disclaimer, the term of this patent is extended or adjusted under 35 U.S.C. 154(b) by 0 days.

(21) Appl. No.: 15/305,127

(22) PCT Filed: Mar. 16, 2015

(86) PCT No.: PCT/JP2015/057657
§ 371 (c)(1),
(2) Date: Oct. 19, 2016

(87) PCT Pub. No.: WO2015/163037
PCT Pub. Date: Oct. 29, 2015

(65) Prior Publication Data
US 2017/0044217 A1 Feb. 16, 2017

(30) Foreign Application Priority Data
Apr. 21, 2014 (JP) .................. 2014-087620

(51) Int. Cl.
*C07K 14/005* (2006.01)
*G01N 33/68* (2006.01)
(Continued)

(52) U.S. Cl.
CPC .......... *C07K 14/005* (2013.01); *A61K 39/235* (2013.01); *C07K 14/00* (2013.01);
(Continued)

(58) Field of Classification Search
None
See application file for complete search history.

(56) References Cited

U.S. PATENT DOCUMENTS 7,858,766 B2 * 12/2010 Pitcovski ............. C07K 14/005
435/235.1
2005/0137156 A1  6/2005 Johnston
(Continued)

FOREIGN PATENT DOCUMENTS

EP           2 397 547      * 12/2011
WO    WO 2004/078977 A1     9/2004
(Continued)

OTHER PUBLICATIONS

O'Shea et al. (Science. Oct. 1991; 254 (5031: 539-54).*
(Continued)

*Primary Examiner* — Shanon A. Foley
(74) *Attorney, Agent, or Firm* — Oblon, McClelland, Maier & Neustadt, L.L.P.

(57) ABSTRACT

The present invention is intended to provide an egg drop syndrome (EDS) vaccine that is capable of effectively preventing EDS and can be stably supplied. The EDS vaccine provided to this end contains as an active ingredient fused protein in which a polypeptide having a coiled-coil forming unit is bound to the knob region in the fiber protein of EDS virus (EDSV).

30 Claims, 6 Drawing Sheets
Specification includes a Sequence Listing.

N: amino-terminus, C: carboxyl-terminus, EDSV Knob: knob region in fiber protein of EDSV, $H_6$: histidine hexamer tag sequence, CMP: trivalent coiled-coil forming unit of CMP protein, GCN4: trivalent coiled-coil forming unit of modified GCN4 protein, Linker A: $(G_4S)_2$ linker sequence, Linker B: $(G_4S)_1$ linker sequence, Linker C: $(G_4S)_2H_6(G_4S)_2$ linker sequence (including histidine hexamer tag sequence), Linker D: $(G_4S)_2H_6(G_4S)_1(G_3S)_1$ linker sequence (including histidine hexamer tag sequence)

(51) Int. Cl.

| | |
|---|---|
| *C12N 7/00* | (2006.01) |
| *C07K 16/08* | (2006.01) |
| *A61K 39/235* | (2006.01) |
| *C07K 16/18* | (2006.01) |
| *C07K 14/00* | (2006.01) |
| *C07K 19/00* | (2006.01) |
| *C07K 14/075* | (2006.01) |
| *C12N 5/10* | (2006.01) |
| *C12N 15/09* | (2006.01) |
| *G01N 33/53* | (2006.01) |
| *A61K 39/00* | (2006.01) |

(52) U.S. Cl.
CPC ............ *C07K 14/075* (2013.01); *C07K 16/08* (2013.01); *C07K 16/081* (2013.01); *C07K 16/18* (2013.01); *C07K 19/00* (2013.01); *C12N 5/10* (2013.01); *C12N 7/00* (2013.01); *C12N 15/09* (2013.01); *G01N 33/53* (2013.01); *G01N 33/6854* (2013.01); *A61K 2039/70* (2013.01); *C07K 2317/34* (2013.01); *C07K 2319/73* (2013.01); *C12N 2710/10134* (2013.01)

(56) References Cited

U.S. PATENT DOCUMENTS

| | | |
|---|---|---|
| 2007/0053935 A1 | 3/2007 | Pitcovski et al. |
| 2012/0100165 A1 | 4/2012 | Arakawa et al. |
| 2017/0044217 A1* | 2/2017 | Yamazaki ............ A61K 39/235 |

FOREIGN PATENT DOCUMENTS

| | | |
|---|---|---|
| WO | WO 2010/092963 A1 | 8/2010 |
| WO | WO 2014/065210 A1 | 5/2014 |

OTHER PUBLICATIONS

Beck et al. (Journal of Molecular Biology. 1996; 256: 909-923).*
Burkhard et al. (Trends in Cellular Biology. Feb. 2001; 11 (2): 82-88).*
Gutter et al. (Avian Pathology. Feb. 2008; 37 (1): 33-37).*
Kim et al. (Biochemistry. Sep. 2013; 52: 7283-7294).*
Sequence alignment of SEQ ID No. 11 with Geneseq database access No. ADR74448 by Pitcovski et al in WO2004078977 on Dec. 2004.*
Harakuni et al (Vaccine. 2016; 34: 3184-3190).*
International Search Report dated Jun. 16, 2015 in PCT/JP2015/057657.
Takeshi Arakawa, et al., "Tricomponent Fusion Complex Comprising a Viral Antigen, a Pentameric α-Helical Coiled-Coil, and an Immunoglobulin-Binding Domain as an Effective Antiviral Vaccine" Vaccine, vol. 32, No. 7, 2013 pp. 864-871.
Kiyotaka Suenaga, et al., "A Recombinant Vaccine Against Egg Drop Syndrome of Chickens" Sci. Rep. Chemo-Sero-Therap. Res. Inst., 2010, vol. 19, pp. 51-60 and cover pages (with English Abstract).
Takeshi Miyata, et al., "Tricomponent Immunopotentiating System as a Novel Molecular Design Strategy for Malaria Vaccine Development" Infection and Immunity, vol. 79, No. 10, 2011, pp. 4260-4275.
Takeshi Arakawa, et al., "Tricomponent Complex Loaded with a Mosquito-Stage Antigen of the Malaria Parasite Induces Potent Transmission-Blocking Immunity" Clinical and Vaccine Immunology, vol. 21, No. 4, 2014, pp. 561-569.
Brian McConnell Adair, et al., "Egg Drop Syndrome" Diseases of Poultry, 12th Edition, 2008, pp. 266-276.
Shigeo Yamaguchi, "Egg Drop Syndrome" Disease of Birds, 7th Edition, 2010 pp. 50-53.

W. Baxendale, et al., "The Results of Field Trials Conducted with an Inactivated Vaccine Against the Egg Drop Syndrome 76 (EDS 76)" Avian Pathology, 9, 1980, pp. 77-91 and cover page.
Fujio Nonaka, et al., "Proliferation and Pathogenicity of Egg Drop Syndrome-1976 (EDS-76) Virus in Cultured Cells and Embryonated Chicken Eggs" Japan Veterinary Medical Association Journal, 37, 1984 pp. 510-515 (with English Summary).
Minoru Higashihara, et al., Isolation of the Virus of Egg Drop Syndrome 1976 (EDS-76), Jpn. J. Vet. Sci., 45, 1983 pp. 603-612.
Michael Hess, et al., "The Complete Nucleotide Sequence of the Egg Drop Syndrome Virus: An Intermediate between Mastadenoviruses and Aviadenoviruses" Virology, 238, 1997, pp. 145-156.
K. Tsukamoto, et al. No Evidence for Adaptation of Current Egg Drop Syndrome 1976 Viruses to Chickens. Avian Diseases, 48, 2004 pp. 220-223.
Celia I. A. Toogood, et al., "Antipeptide Antisera Define Neutralizing Epitopes on the Adenovirus Hexon" Journal of General Virology, 73, 1992, pp. 1429-1435.
Hanne Gahery-Segard, et al., "Immune Response to Recombinant Capsid Proteins of Adenovirus in Humans: Antifiber and Anti-Penton Base Antibodies Have a Synergistic Effect on Neutralizing Activity" Journal of Virology vol. 72, No. 3, 1998, pp. 2388-2397.
Nathalie Louis, et al., "Cell-binding Domain of Adenovirus Serotype 2 Fiber" Journal of Virology, vol. 68, No. 6, 1994, pp. 4104-4106.
Marshall S. Horwitz, "Adenovirus" Fields Virology, 4th Edition, vol. 2, 2001, pp. 2301-2326 and cover pages.
N. M. Green, et al., "Evidence for a Repeating Cross-Beta Sheet Structure in the Adenovirus Fibre" The EMBO Journal, vol. 2, No. 8, 1983, pp. 1357-1365.
Saw See Hong, et al., "Protein Ligands of the Human Adenovirus Type 2 Outer Capsid Identified by Biopanning of a Phage-Displayed Peptide Library on Separate Domains of Wild-Type and Mutant Penton Capsomers" The EMBO Journal, vol. 14, No. 19, 1995, pp. 4714-4727.
Lynda J. Henry, et al., "Characterization of the Knob Domain of the Adenovirus Type 5 Fiber Protein Expressed in *Escherichia coli*" Journal of Virology, vol. 68, No. 8, 1994, pp. 5239-5246.
Mark J. Van Raaij, et al., "A triple Beta-Spiral in the Adenovirus Fibre Shaft Reveals a New Structural Motif for a Fibrous Protein" Nature, vol. 401, 1999 pp. 935-938.
Pieter F. W. Stouten, et al., "New Triple-Helical Model for the Shaft of the Adenovirus Fibre." J. Mol. Biol., 226, 1992, pp. 1073-1084.
D. Xia, et al., "Structure of the Receptor Binding Domain of Adenovirus Type 5 Fiber Protein" Curr. Top Microbiol. Immunol., 199, 1995, pp. 39-46.
Dmitry M. Shayakhmetov, et al., "Dependence of Adenovirus Infectivity on Length of the Fiber Shaft Domain" Journal of Virology, vol. 74, No. 22, 2000, pp. 10274-10286.
B. Gutter, et al., "Recombinant Egg Drop Syndrome Subunit Vaccine Offers an Alternative to Virus Propagation in Duck Eggs" Avian Pathology, 37, 2008, pp. 33-37 and cover page.
E. Fingerut, et al., "A subunit Vaccine Against the Adenovirus Egg-Drop Syndrome Using Part of its Fiber Protein" Vaccine, 21, 2003, pp. 2761-2766.
Andrei N. Lupas, et al. "The Structure of α-Helical Coiled Coils" Advances in Protein Chemistry, vol. 70, 2005, pp. 37-78.
Extended European Search Report dated Nov. 24, 2017 in Patent Application No. 15783019.1, citing documents AW-AY therein, 8 pages.
Reema Zeineldin, et al. "Oligomeric forms of the 148 kDa cartilage matrix protein", The Biochemical Journal, vol. 328, XP002775439, 1997, pp. 665-668.
Juan A. Cooper, et al. "Mapping of Conformational B Cell Epitopes Within Alpha-Helical Coiled Coil Proteins", Molecular Pharmacology, vol. 34, No. 6, XP000916165, 1997, pp. 433-440.
Tetsuya Harakuni, et al. "Fiber knob domain lacking the shaft sequence but fused to a coiled coil is a candidate subunit vaccine against egg-drop syndrome", Vaccine, vol. 34, No. 27, XP029569612, 2016, pp. 3184-3190.

* cited by examiner

Fig.1

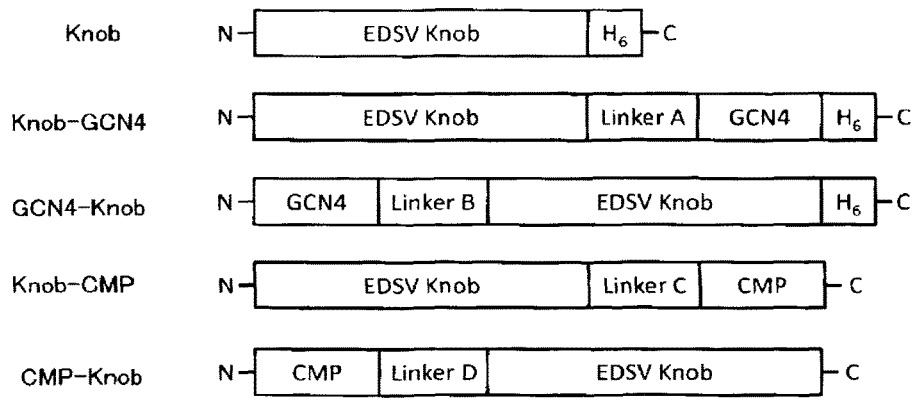

N: amino-terminus, C: carboxyl-terminus, EDSV Knob: knob region in fiber protein of EDSV, $H_6$: histidine hexamer tag sequence, CMP: trivalent coiled-coil forming unit of CMP protein, GCN4: trivalent coiled-coil forming unit of modified GCN4 protein, Linker A: $(G_4S)_2$ linker sequence, Linker B: $(G_4S)_1$ linker sequence, Linker C: $(G_4S)_2H_6(G_4S)_2$ linker sequence (including histidine hexamer tag sequence), Linker D: $(G_4S)_2H_6(G_4S)_1(G_3S)_1$ linker sequence (including histidine hexamer tag sequence)

Fig

SEQUENCE LISTING

<160> NUMBER OF SEQ ID NOS: 33

<210> SEQ ID NO 1
<211> LENGTH: 219
<212> TYPE: PRT
<213> ORGANISM: Eggdrop syndrome virus

<400> SEQUENCE: 1

```
Met Thr Pro Leu Thr Arg Ile Ile Ser Met Gly Asn Asn Leu Phe Asp
1               5                   10                  15

Ser Gly Tyr Glu Ile Phe Ala Ser Cys Pro Gln Asn Lys Ala Ala Lys
            20                  25                  30

Val Ala Gly Tyr Val Tyr Leu Thr Ser Val Gly Gly Leu Val His Gly
        35                  40                  45

Thr Ile Gln Ile Lys Ala Thr Ala Gly Tyr Trp Phe Thr Gly Gly Asn
    50                  55                  60

Ser Val Gln Glu Ser Ile Arg Phe Gly Leu Val Leu Cys Pro Phe Ser
65                  70                  75                  80

Ala Arg Asp Pro Thr Ala Asn Leu Ser Gly Trp Pro Ala Pro Val Val
                85                  90                  95

Trp Ser Gly Asp Ser Asn Thr Pro Leu Tyr Phe Ala Ala Asn Ala Ile
            100                 105                 110

Ser Tyr Thr Asn Asn Arg Val Asn Leu Ala Val Thr Gly Asn Phe Tyr
        115                 120                 125

Lys Glu Glu Thr Glu Leu Pro Gly Tyr Thr Arg His Ser Phe Cys Pro
    130                 135                 140

Thr Gly Thr Thr Gly Met Asn Phe Thr Gly Gly Asn Leu Tyr Val Cys
145                 150                 155                 160

Pro Cys Thr Val Asn Thr Gly Ala Thr Thr Leu Asn Ala Ile Tyr Met
                165                 170                 175

Val Phe Val Ile Thr Gln Ser Ala Leu Gly Thr Asn Phe Phe Ala Ser
            180                 185                 190

Asn Thr Pro Pro Asn Thr Phe Phe Leu Thr Pro Pro Ile Pro Phe Thr
        195                 200                 205

Tyr Val Gly Ala Gln His His His His His
    210                 215
```

-continued

<210> SEQ ID NO 2
<211> LENGTH: 669
<212> TYPE: DNA
<213> ORGANISM: Artificial Sequence
<220> FEATURE:
<223> OTHER INFORMATION: Modified for E. coli expression

<400> SEQUENCE: 2

```
catatgaccc cgctgacccg cattatcagc atgggcaaca atctctttga ctccggctat      60
gagattttg cgagctgccc acaaaataaa gcggccaaag ttgcaggcta cgtgtatctc     120
accagtgttg gtggcttggt ccacggcacc attcaaatca agcaacggc cggctactgg     180
tttacgggtg ggaactcggt gcaggaaagc attcgctttg gtcttgtgtt atgcccgttt     240
tcggcgcgtg atccgaccgc aaatttatcg ggttggccgg ctccggtagt ttggtccggc     300
gattctaaca caccgctgta ttttgcggcg aacgcgattt cttatacgaa taaccgtgtg     360
aacctggccg ttacgggcaa tttctataag gaggaaaccg aactgcctgg gtatactcgc     420
catagttct gcccgaccgg caccaccggc atgaatttta ctggtggtaa cttgtatgtg     480
tgtccttgta ctgtcaatac aggcgctacg acgctgaatg ctatctacat ggtgtttgtc     540
atcacacaga gcgccctggg gactaatttc ttcgcatcga ataccccgcc aaacaccttt     600
ttccttacgc cgccaatccc gttcacctat gtaggggccc agcatcatca tcaccaccac     660
taaggatcc                                                             669
```

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
caaccatgga aggagaggtg gaaatta      27

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ccgctcgagc tactgtgctc caac      24

<210> SEQ ID NO 5
<211> LENGTH: 339
<212> TYPE: PRT
<213> ORGANISM: Eggdrop syndrome virus

<400> SEQUENCE: 5

```
Met Glu Gly Glu Val Glu Ile Lys Asn Pro Arg Asn Pro Ile Gly Leu
1               5                   10                  15

Thr Gln Asp Gly Glu Leu Ala Leu Ile Ile Gly Tyr Gly Leu Thr Thr
            20                  25                  30

Leu Asp Gly Arg Leu Thr Leu Leu Thr Ala Ser Thr Ser Pro Ile Ala
        35                  40                  45

Val Gly Pro Thr Gly Val Thr Phe Asn Val Thr Pro Ser Asp Phe Tyr
    50                  55                  60

Phe Leu Ser Ser Lys Leu Ala Leu Asn Val Glu Thr Arg Gly Gly Leu
65                  70                  75                  80
```

```
Glu Lys Ser Asp Thr Gly Leu Lys Ile Lys Arg Ala Ala Pro Leu Ser
                85                  90                  95

Ile Thr Ser Asp Gly Glu Leu Thr Leu Ala Tyr Asp Ser Thr Asp Phe
            100                 105                 110

Gln Val Thr Glu Asn Gly Leu Ala Leu Lys Val Ser Pro Thr Gln Thr
        115                 120                 125

Pro Leu Thr Arg Ile Ile Ser Met Gly Asn Asn Leu Phe Asp Ser Gly
    130                 135                 140

Tyr Glu Ile Phe Ala Ser Cys Pro Gln Asn Lys Ala Ala Lys Val Ala
145                 150                 155                 160

Gly Tyr Val Tyr Leu Thr Ser Val Gly Leu Val His Gly Thr Ile
                165                 170                 175

Gln Ile Lys Ala Thr Ala Gly Tyr Trp Phe Thr Gly Gly Asn Ser Val
            180                 185                 190

Gln Glu Ser Ile Arg Phe Gly Leu Val Leu Cys Pro Phe Ser Ala Arg
        195                 200                 205

Asp Pro Thr Ala Asn Leu Ser Gly Trp Pro Ala Pro Val Val Trp Ser
    210                 215                 220

Gly Asp Ser Asn Thr Pro Leu Tyr Phe Ala Ala Asn Ala Ile Ser Tyr
225                 230                 235                 240

Thr Asn Asn Arg Val Asn Leu Ala Val Thr Gly Asn Phe Tyr Lys Glu
                245                 250                 255

Glu Thr Glu Leu Pro Gly Tyr Thr Arg His Ser Phe Cys Pro Thr Gly
            260                 265                 270

Thr Thr Gly Met Asn Phe Thr Gly Gly Asn Leu Tyr Val Cys Pro Cys
        275                 280                 285

Thr Val Asn Thr Gly Ala Thr Thr Leu Asn Ala Ile Tyr Met Val Phe
    290                 295                 300

Val Ile Thr Gln Ser Ala Leu Gly Thr Asn Phe Phe Ala Ser Asn Thr
305                 310                 315                 320

Pro Pro Asn Thr Phe Phe Leu Thr Pro Pro Ile Pro Phe Thr Tyr Val
                325                 330                 335

Gly Ala Gln

<210> SEQ ID NO 6
<211> LENGTH: 1014
<212> TYPE: DNA
<213> ORGANISM: Eggdrop syndrome virus

<400> SEQUENCE: 6
ggagaggtgg aaattaaaaa ccctagaaac cccataggcc tgacccaaga tggtgaattg    60
gctttgataa tcggttatgg cctaacaacc cttgatggac ggctcactct acttaccgct   120
tcgacctctc cgatagctgt agggccaacc ggtgttacat ttaatgttac accgagtgat   180
ttttactttt tatctagtaa attagctctc aatgttgaga cccgtggcgg cttagaaaaa   240
agtgacactg gtttaaaaat taaacgtgcg gcccctctca gtatcacatc tgatggtgag   300
ttgactttgg cttatgattc cacggatttt caggtgacag aaaacggtct ggccctaaag   360
gtatctccga cgcagacccc tctcaccaga taatttcta tgggaaataa cttgtttgat   420
tctggttatg agatttttgc ttcatgtccg cagaacaaag cagcaaaggt tgcagggtat   480
gtgtatttaa catcggttgg tgggcttgta catgggacca ttcagattaa agctactgcg   540
gggtattggt ttacgggggg aaacagcgtg caggaaagta tcaggtttgg attggtgttg   600
tgtcctttta gtgctcgcga ccccactgct aacctgtcag gctggccagc gccagtagtg   660
```

```
tggagtggtg atagcaatac tcccctatat tttgcggcca atgccattag ttataccaat    720
aaccgtgtaa atcttgcagt taccggtaac ttttacaagg aggaaaccga attgccgggt    780
tacactcgtc attctttctg ccctaccggg accaccggaa tgaattttac aggggtaat    840 ttgtatgtgt gtccgtgcac tgtaaataca ggggccacca cactgaatgc catttatatg    900
gtgtttgtga ttactcaatc agctttggga actaatttct tgcttctaa caccccctccc    960 aacacattct ttttaactcc ccccattccc tttacatatg ttggagcaca gtag          1014

<210> SEQ ID NO 7
<211> LENGTH: 41
<212> TYPE: PRT
<213> ORGANISM: Artificial Sequence
<220> FEATURE:
<223> OTHER INFORMATION: (G4S)2-GCN4

<400> SEQUENCE: 7

Met Gly Gly Gly Gly Ser Gly Gly Gly Gly Ser Arg Met Lys Gln Ile
1               5                   10                  15

Glu Asp Lys Ile Glu Glu Ile Glu Ser Lys Gln Lys Lys Ile Glu Asn
            20                  25                  30

Glu Ile Ala Arg Ile Lys Lys Leu Glu
        35                  40

<210> SEQ ID NO 8
<211> LENGTH: 125
<212> TYPE: DNA
<213> ORGANISM: Artificial Sequence
<220> FEATURE:
<223> OTHER INFORMATION: (G4S)2-GCN4

<400> SEQUENCE: 8
ccatgggcgg tggcggcagc ggcggtggcg gcagccgcat gaaacagatt gaagataaaa    60
ttgaagaaat cgaaagcaaa cagaaaaaaa ttgaaaatga aattgcccgt atcaaaaaac    120
tcgag                                                                125

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
gcgccatggg caccccctctc accagaataa tttctatgg                          39

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
gcgccatggt ctgtgctcca acatatgtaa agggaatgg                           39

<210> SEQ ID NO 11
<211> LENGTH: 212
<212> TYPE: PRT
<213> ORGANISM: Eggdrop syndrome virus
```

<400> SEQUENCE: 11

```
Thr Pro Leu Thr Arg Ile Ile Ser Met Gly Asn Asn Leu Phe Asp Ser
1               5                   10                  15
Gly Tyr Glu Ile Phe Ala Ser Cys Pro Gln Asn Lys Ala Ala Lys Val
            20                  25                  30
Ala Gly Tyr Val Tyr Leu Thr Ser Val Gly Gly Leu Val His Gly Thr
        35                  40                  45
Ile Gln Ile Lys Ala Thr Ala Gly Tyr Trp Phe Thr Gly Gly Asn Ser
    50                  55                  60
Val Gln Glu Ser Ile Arg Phe Gly Leu Val Leu Cys Pro Phe Ser Ala
65                  70                  75                  80
Arg Asp Pro Thr Ala Asn Leu Ser Gly Trp Pro Ala Pro Val Val Trp
                85                  90                  95
Ser Gly Asp Ser Asn Thr Pro Leu Tyr Phe Ala Ala Asn Ala Ile Ser
            100                 105                 110
Tyr Thr Asn Asn Arg Val Asn Leu Ala Val Thr Gly Asn Phe Tyr Lys
        115                 120                 125
Glu Glu Thr Glu Leu Pro Gly Tyr Thr Arg His Ser Phe Cys Pro Thr
    130                 135                 140
Gly Thr Thr Gly Met Asn Phe Thr Gly Gly Asn Leu Tyr Val Cys Pro
145                 150                 155                 160
Cys Thr Val Asn Thr Gly Ala Thr Thr Leu Asn Ala Ile Tyr Met Val
                165                 170                 175
Phe Val Ile Thr Gln Ser Ala Leu Gly Thr Asn Phe Phe Ala Ser Asn
            180                 185                 190
Thr Pro Pro Asn Thr Phe Phe Leu Thr Pro Ile Pro Phe Thr Tyr
        195                 200                 205
Val Gly Ala Gln
    210
```

<210> SEQ ID NO 12
<211> LENGTH: 636
<212> TYPE: DNA
<213> ORGANISM: Eggdrop syndrome virus

<400> SEQUENCE: 12

```
acccctctca ccagaataat ttctatggga aataacttgt ttgattctgg ttatgagatt      60
tttgcttcat gtccgcagaa caaagcagca aaggttgcag ggtatgtgta tttaacatcg     120
gttggtgggc ttgtacatgg gaccattcag attaaagcta ctgcggggta ttggtttacg     180
gggggaaaca gcgtgcagga aagtatcagg tttggattgg tgttgtgtcc ttttagtgct     240
cgcgacccca ctgctaacct gtcaggctgg ccagcgccag tagtgtggag tggtgatagc     300
aatactcccc tatattttgc ggccaatgcc attagttata ccaataaccg tgtaaatctt     360
gcagttaccg gtaactttta caaggaggaa accgaattgc cgggttacac tcgtcattct     420
ttctgcccta ccgggaccac cggaatgaat tttacagggg gtaatttgta tgtgtgtccg     480
tgcactgtaa atacaggggc caccacactg aatgccattt atatggtgtt tgtgattact     540
caatcagctt tgggaactaa tttctttgct tctaacaccc ctcccaacac attcttttta     600
actcccccca ttccctttac atatgttgga gcacag                               636
```

<210> SEQ ID NO 13
<211> LENGTH: 262
<212> TYPE: PRT
<213> ORGANISM: Artificial Sequence
<220> FEATURE:
<223> OTHER INFORMATION: Knob-GCN4

<400> SEQUENCE: 13

```
Met Gly Thr Pro Leu Thr Arg Ile Ile Ser Met Gly Asn Asn Leu Phe
1               5                   10                  15

Asp Ser Gly Tyr Glu Ile Phe Ala Ser Cys Pro Gln Asn Lys Ala Ala
            20                  25                  30

Lys Val Ala Gly Tyr Val Tyr Leu Thr Ser Val Gly Gly Leu Val His
        35                  40                  45

Gly Thr Ile Gln Ile Lys Ala Thr Ala Gly Tyr Trp Phe Thr Gly Gly
    50                  55                  60

Asn Ser Val Gln Glu Ser Ile Arg Phe Gly Leu Val Leu Cys Pro Phe
65                  70                  75                  80

Ser Ala Arg Asp Pro Thr Ala Asn Leu Ser Gly Trp Pro Ala Pro Val
                85                  90                  95

Val Trp Ser Gly Asp Ser Asn Thr Pro Leu Tyr Phe Ala Ala Asn Ala
            100                 105                 110

Ile Ser Tyr Thr Asn Asn Arg Val Asn Leu Ala Val Thr Gly Asn Phe
        115                 120                 125

Tyr Lys Glu Glu Thr Glu Leu Pro Gly Tyr Thr Arg His Ser Phe Cys
    130                 135                 140

Pro Thr Gly Thr Thr Gly Met Asn Phe Thr Gly Gly Asn Leu Tyr Val
145                 150                 155                 160

Cys Pro Cys Thr Val Asn Thr Gly Ala Thr Thr Leu Asn Ala Ile Tyr
                165                 170                 175

Met Val Phe Val Ile Thr Gln Ser Ala Leu Gly Thr Asn Phe Phe Ala
            180                 185                 190

Ser Asn Thr Pro Pro Asn Thr Phe Phe Leu Thr Pro Pro Ile Pro Phe
        195                 200                 205

Thr Tyr Val Gly Ala Gln Thr Met Gly Gly Gly Ser Gly Gly Gly
    210                 215                 220

Gly Ser Arg Met Lys Gln Ile Glu Asp Lys Ile Glu Glu Ile Glu Ser
225                 230                 235                 240

Lys Gln Lys Lys Ile Glu Asn Glu Ile Ala Arg Ile Lys Lys Leu Glu
                245                 250                 255

His His His His His His
            260
```

<210> SEQ ID NO 14
<211> LENGTH: 789
<212> TYPE: DNA
<213> ORGANISM: Artificial Sequence
<220> FEATURE:
<223> OTHER INFORMATION: Knob-GCN4

<400> SEQUENCE: 14

```
atgggcaccc ctctcaccag aataatttct atgggaaata acttgtttga ttctggttat      60 gagattttg cttcatgtcc gcagaacaaa gcagcaaagg ttgcagggta tgtgtattta     120
acatcggttg gtgggcttgt acatgggacc attcagatta aagctactgc ggggtattgg    180
tttacggggg gaaacagcgt gcaggaaagt atcaggtttg gattggtgtt gtgtcctttt    240
agtgctcgcg accccactgc taacctgtca ggctggccag cgccagtagt gtggagtggt    300
gatagcaata ctcccctata ttttgcggcc aatgccatta gttataccaa taaccgtgta    360
aatcttgcag ttaccggtaa cttttacaag gaggaaaccg aattgccggg ttacactcgt    420
```

```
cattctttct gccctaccgg gaccaccgga atgaattta caggggtaa tttgtatgtg      480 tgtccgtgca ctgtaaatac aggggccacc acactgaatg ccatttatat ggtgtttgtg      540
attactcaat cagctttggg aactaatttc tttgcttcta acaccccctcc caacacattc     600 ttttaactc cccccattcc ctttacatat gttggagcac agaccatggg cggtggcggc       660
agcggcggtg gcggcagccg catgaaacag attgaagata aaattgaaga aatcgaaagc      720
aaacagaaaa aaattgaaaa tgaaattgcc cgtatcaaaa aactcgagca ccaccaccac      780
caccactga                                                               789

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gcgccatggg ccgcatgaaa cagattgaag ataaaattga ag                          42

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
ggctcgaggc tgccgccacc gccttccagt tttttgatac gggcaatttc                  50

<210> SEQ ID NO 17
<211> LENGTH: 39
<212> TYPE: PRT
<213> ORGANISM: Artificial Sequence
<220> FEATURE:
<223> OTHER INFORMATION: GCN4-(G4S)1

<400> SEQUENCE: 17

Met Gly Arg Met Lys Gln Ile Glu Asp Lys Ile Glu Glu Ile Glu Ser
1               5                   10                  15

Lys Gln Lys Lys Ile Glu Asn Glu Ile Ala Arg Ile Lys Lys Leu Glu
            20                  25                  30

Gly Gly Gly Gly Ser Leu Glu
        35

<210> SEQ ID NO 18
<211> LENGTH: 124
<212> TYPE: DNA
<213> ORGANISM: Artificial Sequence
<220> FEATURE:
<223> OTHER INFORMATION: GCN4-(G4S)1

<400> SEQUENCE: 18
gcgccatggg ccgcatgaaa cagattgaag ataaaattga agaaatcgaa agcaaacaga       60
aaaaaattga aatgaaatt gcccgtatca aaaaactgga aggcggtggc ggcagcctcg       120
agcc                                                                    124

<210> SEQ ID NO 19
<211> LENGTH: 36
<212> TYPE: DNA
<213> ORGANISM: Artificial Sequence
```

<220> FEATURE:
<223> OTHER INFORMATION: primer

<400> SEQUENCE: 19
ggctcgagac ccctctcacc agaataattt ctatgg       36

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
ggctcgagct gtgctccaac atatgtaaag ggaatgg       37

<210> SEQ ID NO 21
<211> LENGTH: 269
<212> TYPE: PRT
<213> ORGANISM: Artificial Sequence
<220> FEATURE:
<223> OTHER INFORMATION: GCN4-Knob

<400> SEQUENCE: 21

Met Gly Arg Met Lys Gln Ile Glu Asp Lys Ile Glu Glu Ile Glu Ser
1               5                   10                  15
Lys Gln Lys Lys Ile Glu Asn Glu Ile Ala Arg Ile Lys Lys Leu Glu
            20                  25                  30
Gly Gly Gly Gly Ser Leu Glu Thr Pro Leu Thr Arg Ile Ile Ser Met
        35                  40                  45
Gly Thr Pro Leu Thr Arg Ile Ile Ser Met Gly Asn Asn Leu Phe Asp
    50                  55                  60
Ser Gly Tyr Glu Ile Phe Ala Ser Cys Pro Gln Asn Lys Ala Ala Lys
65                  70                  75                  80
Val Ala Gly Tyr Val Tyr Leu Thr Ser Val Gly Gly Leu Val His Gly
                85                  90                  95
Thr Ile Gln Ile Lys Ala Thr Ala Gly Tyr Trp Phe Thr Gly Gly Asn
            100                 105                 110
Ser Val Gln Glu Ser Ile Arg Phe Gly Leu Val Leu Cys Pro Phe Ser
        115                 120                 125
Ala Arg Asp Pro Thr Ala Asn Leu Ser Gly Trp Pro Ala Pro Val Val
    130                 135                 140
Trp Ser Gly Asp Ser Asn Thr Pro Leu Tyr Phe Ala Ala Asn Ala Ile
145                 150                 155                 160
Ser Tyr Thr Asn Asn Arg Val Asn Leu Ala Val Thr Gly Asn Phe Tyr
                165                 170                 175
Lys Glu Glu Thr Glu Leu Pro Gly Tyr Thr Arg His Ser Phe Cys Pro
            180                 185                 190
Thr Gly Thr Thr Gly Met Asn Phe Thr Gly Gly Asn Leu Tyr Val Cys
        195                 200                 205
Pro Cys Thr Val Asn Thr Gly Ala Thr Thr Leu Asn Ala Ile Tyr Met
    210                 215                 220
Val Phe Val Ile Thr Gln Ser Ala Leu Gly Thr Asn Phe Phe Ala Ser
225                 230                 235                 240
Asn Thr Pro Pro Asn Thr Phe Phe Leu Thr Pro Ile Pro Phe Thr
                245                 250                 255
Tyr Val Gly Ala Gln Leu Glu His His His His His
            260                 265

<210> SEQ ID NO 22
<211> LENGTH: 780
<212> TYPE: DNA
<213> ORGANISM: Artificial Sequence
<220> FEATURE:
<223> OTHER INFORMATION: GCN4-Knob

<400> SEQUENCE: 22

```
atgggccgca tgaaacagat tgaagataaa attgaagaaa tcgaaagcaa acagaaaaaa      60
attgaaaatg aaattgcccg tatcaaaaaa ctggaaggcg gtggcggcag cctcgagacc     120
cctctcacca gaataaattc tatgggaaat aacttgtttg attctggtta tgagattttt     180
gcttcatgtc cgcagaacaa agcagcaaag gttgcaggt atgtgtattt aacatcggtt      240
ggtgggcttg tacatgggac cattcagatt aaagctactg cggggtattg gtttacgggg     300
ggaaacagcg tgcaggaaag tatcaggttt ggattggtgt tgtgtccttt tagtgctcgc     360
gaccccactg ctaacctgtc aggctggcca gcgccagtag tgtggagtgg tgatagcaat     420
actccctat attttgcggc caatgccatt agttatacca ataaccgtgt aaatcttgca     480
gttaccggta acttttacaa ggaggaaacc gaattgccgg ttacactcg tcattctttc      540
tgccctaccg ggaccaccgg aatgaatttt acaggggta atttgtatgt gtgtccgtgc      600
actgtaaata caggggccac cacactgaat gccatttata tggtgtttgt gattactcaa     660
tcagctttgg gaactaattt ctttgcttct aacacccctc ccaacacatt cttttaact      720
ccccccattc cctttacata tgttggagca cagctcgagc accaccacca ccaccactga     780
```

<210> SEQ ID NO 23
<211> LENGTH: 284
<212> TYPE: PRT
<213> ORGANISM: Artificial Sequence
<220> FEATURE:
<223> OTHER INFORMATION: Knob-CMP

<400> SEQUENCE: 23

```
Met Thr Pro Leu Thr Arg Ile Ile Ser Met Gly Asn Asn Leu Phe Asp
  1               5                  10                  15

Ser Gly Tyr Glu Ile Phe Ala Ser Cys Pro Gln Asn Lys Ala Ala Lys
             20                  25                  30

Val Ala Gly Tyr Val Tyr Leu Thr Ser Val Gly Gly Leu Val His Gly
         35                  40                  45

Thr Ile Gln Ile Lys Ala Thr Ala Gly Tyr Trp Phe Thr Gly Gly Asn
     50                  55                  60

Ser Val Gln Glu Ser Ile Arg Phe Gly Leu Val Leu Cys Pro Phe Ser
 65                  70                  75                  80

Ala Arg Asp Pro Thr Ala Asn Leu Ser Gly Trp Pro Ala Pro Val Val
                 85                  90                  95

Trp Ser Gly Asp Ser Asn Thr Pro Leu Tyr Phe Ala Ala Asn Ala Ile
            100                 105                 110

Ser Tyr Thr Asn Asn Arg Val Asn Leu Ala Val Thr Gly Asn Phe Tyr
        115                 120                 125

Lys Glu Glu Thr Glu Leu Pro Gly Tyr Thr Arg His Ser Phe Cys Pro
    130                 135                 140

Thr Gly Thr Thr Gly Met Asn Phe Thr Gly Gly Asn Leu Tyr Val Cys
145                 150                 155                 160

Pro Cys Thr Val Asn Thr Gly Ala Thr Thr Leu Asn Ala Ile Tyr Met
                165                 170                 175
```

Val Phe Val Ile Thr Gln Ser Ala Leu Gly Thr Asn Phe Phe Ala Ser
                180                 185                 190

Asn Thr Pro Pro Asn Thr Phe Phe Leu Thr Pro Ile Pro Phe Thr
            195                 200                 205

Tyr Val Gly Ala Gln Gly Thr Gly Gly Gly Ser Gly Gly Gly Gly
        210                 215                 220

Ser His His His His His Gly Gly Gly Ser Gly Gly Gly Gly
225                 230                 235                 240

Ser Glu Glu Asp Pro Cys Glu Cys Lys Ser Ile Val Lys Phe Gln Thr
                245                 250                 255

Lys Val Glu Glu Leu Ile Asn Thr Leu Gln Gln Lys Leu Glu Ala Val
                260                 265                 270

Ala Lys Arg Ile Glu Ala Leu Glu Asn Lys Ile Ile
        275                 280

<210> SEQ ID NO 24
<211> LENGTH: 904
<212> TYPE: DNA
<213> ORGANISM: Artificial Sequence
<220> FEATURE:
<223> OTHER INFORMATION: Knob-CMP

<400> SEQUENCE: 24
actttaagaa ggagatatac atatgacccc gctgacccgt atcattagta tgggcaataa    60
cctgttcgac tctggctatg aaatcttcgc ctcgtgtccg caaaataaag cagccaaagt   120
ggcaggctat gtttatctga ccagcgtggg cggtctggtt catggcacga ttcagatcaa   180
agcaaccgcg ggttattggt ttacgggcgg taatagtgtg caagaatcta ttcgctttgg   240
cctggtgctg tgcccgttct ctgcacgtga tccgaccgca aacctgtccg gctggccggc   300
accggtggtt tggagcggtg actcgaatac cccgctgtat tttgcggcca acgcgatcag   360
ttataccaat aaccgcgtga atctggccgt taccggcaac ttctataaag aagagaccga   420
gctgccgggt tatacgcgtc actcgttttg tccgaccggc accacgggta tgaatttcac   480
gggcggtaac ctgtatgtgt gcccgtgtac cgttaatacg ggcgcaacca cgctgaacgc   540
gatttatatg gtgtttgtta tcacccagag cgccctgggc acgaatttct ttgcatcgaa   600
taccccgccg aacacgtttt tcctgacccc gccgattccg ttcacctatg tgggcgccca   660
gggtaccggc ggtggcggtt ccggcggtgg cggtagccat caccatcacc atcacgcgg   720
tggcggttcg ggcggtggcg gtagtgaaga agatccgtgc gaatgtaaaa gcattgtgaa   780
atttcagacc aaagttgaag agctgatcaa taccctgcag cagaaactgg aggcggttgc   840
caaacgcatt gaagcactgg agaataaaat catctaagga tccggctgct aacaaagccc   900
gaaa                                                                904

<210> SEQ ID NO 25
<211> LENGTH: 283
<212> TYPE: PRT
<213> ORGANISM: Artificial Sequence
<220> FEATURE:
<223> OTHER INFORMATION: CMP-Knob

<400> SEQUENCE: 25

Met Glu Glu Asp Pro Cys Glu Cys Lys Ser Ile Val Lys Phe Gln Thr
1               5                   10                  15

Lys Val Glu Glu Leu Ile Asn Thr Leu Gln Gln Lys Leu Glu Ala Val
            20                  25                  30

Ala Lys Arg Ile Glu Ala Leu Glu Asn Lys Ile Ile Gly Gly Gly
            35                  40                  45

Ser Gly Gly Gly Ser His His His His His Gly Gly Gly Gly
 50                  55                  60

Ser Gly Gly Ser Gly Thr Thr Pro Leu Thr Arg Ile Ile Ser Met
 65                  70                  75                  80

Gly Asn Asn Leu Phe Asp Ser Gly Tyr Glu Ile Phe Ala Ser Cys Pro
                85                  90                  95

Gln Asn Lys Ala Ala Lys Val Ala Gly Tyr Val Tyr Leu Thr Ser Val
            100                 105                 110

Gly Gly Leu Val His Gly Thr Ile Gln Ile Lys Ala Thr Ala Gly Tyr
            115                 120                 125

Trp Phe Thr Gly Gly Asn Ser Val Gln Glu Ser Ile Arg Phe Gly Leu
130                 135                 140

Val Leu Cys Pro Phe Ser Ala Arg Asp Pro Thr Ala Asn Leu Ser Gly
145                 150                 155                 160

Trp Pro Ala Pro Val Val Trp Ser Gly Asp Ser Asn Thr Pro Leu Tyr
                165                 170                 175

Phe Ala Ala Asn Ala Ile Ser Tyr Thr Asn Asn Arg Val Asn Leu Ala
            180                 185                 190

Val Thr Gly Asn Phe Tyr Lys Glu Glu Thr Glu Leu Pro Gly Tyr Thr
        195                 200                 205

Arg His Ser Phe Cys Pro Thr Gly Thr Gly Met Asn Phe Thr Gly
    210                 215                 220

Gly Asn Leu Tyr Val Cys Pro Cys Thr Val Asn Thr Gly Ala Thr Thr
225                 230                 235                 240

Leu Asn Ala Ile Tyr Met Val Phe Val Ile Thr Gln Ser Ala Leu Gly
                245                 250                 255

Thr Asn Phe Phe Ala Ser Asn Thr Pro Pro Asn Thr Phe Phe Leu Thr
            260                 265                 270

Pro Pro Ile Pro Phe Thr Tyr Val Gly Ala Gln
        275                 280

<210> SEQ ID NO 26
<211> LENGTH: 898
<212> TYPE: DNA
<213> ORGANISM: Artificial Sequence
<220> FEATURE:
<223> OTHER INFORMATION: CMP-Knob

<400> SEQUENCE: 26

```
ttaagaagga gatatacata tggaagaaga cccgtgtgag tgtaaaagca ttgtgaaatt      60
ccaaacgaaa gtggaagaac tgattaatac cctgcaacag aaactggagg ccgtggcaaa     120
acgcattgaa gcgctggaga ataaaattat cggcggtggc ggttcgggcg gtggcggtag     180
tcatcaccat caccatcacg gcggtggcgg tagtggcggt ggctctggta ccacgccgct     240
gacccgtatt atctcgatgg gtaataacct gtttgattct ggctatgaaa tcttcgcatc     300
ctgcccgcag aataaagcgg ccaaagtggc gggctatgtt tatctgacca gcgtgggtgg     360
cctggttcat ggcaccattc agatcaaagc gacggccggc tattggttta ccggtggcaa     420
ttccgtgcaa gagagcattc gctttggcct ggtgctgtgt ccgttcagcg cacgtgatcc     480
gaccgcaaac ctgtcgggtt ggccggcacc ggtggtttgg agcggcgact cgaataccccc     540
gctgtatttt gcagcgaacg ccatcagtta cgaataaac cgcgtgaatc tggcagttac     600
cggtaacttc tataaagaag agacggaact gccgggctat acccgtcaca gcttttgccc     660
```

```
gacgggcacc acgggcatga atttcaccgg tggcaacctg tatgtgtgcc cgtgtaccgt    720
taatacgggt gccaccacgc tgaacgcaat ttatatggtg tttgttatca cgcaaagtgc    780
gctgggcacc aatttctttg cctctaacac cccgccgaac acgttttcc tgacgccgcc     840 gattccgttt acctatgtgg gtgcgcaata aggatccggc tgctaacaaa gcccgaaa      898
```

<210> SEQ ID NO 27
<211> LENGTH: 29
<212> TYPE: PRT
<213> ORGANISM: Yeast

<400> SEQUENCE: 27

```
Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu
            20                  25
```

<210> SEQ ID NO 28
<211> LENGTH: 29
<212> TYPE: PRT
<213> ORGANISM: Artificial Sequence
<220> FEATURE:
<223> OTHER INFORMATION: GCN4-pII

<400> SEQUENCE: 28

```
Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu
            20                  25
```

<210> SEQ ID NO 29
<211> LENGTH: 29
<212> TYPE: PRT
<213> ORGANISM: Artificial Sequence
<220> FEATURE:
<223> OTHER INFORMATION: GCN4-pIQI

<400> SEQUENCE: 29

```
Arg Met Lys Gln Ile Glu Asp Lys Ile Glu Glu Ile Leu Ser Lys Gln
1               5                   10                  15

Tyr His Ile Glu Asn Glu Ile Ala Arg Ile Lys Lys Leu
            20                  25
```

<210> SEQ ID NO 30
<211> LENGTH: 29
<212> TYPE: PRT
<213> ORGANISM: Artificial Sequence
<220> FEATURE:
<223> OTHER INFORMATION: IQN17

<400> SEQUENCE: 30

```
Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu
            20                  25
```

<210> SEQ ID NO 31
<211> LENGTH: 43
<212> TYPE: PRT
<213> ORGANISM: Gallus gallus -continued

```
<400> SEQUENCE: 31

Glu Glu Asp Pro Cys Glu Cys Lys Ser Ile Val Lys Phe Gln Thr Lys
1               5                   10                  15

Val Glu Glu Leu Ile Asn Thr Leu Gln Gln Lys Leu Glu Ala Val Ala
            20                  25                  30

Lys Arg Ile Glu Ala Leu Glu Asn Lys Ile Ile
        35                  40

<210> SEQ ID NO 32
<211> LENGTH: 129
<212> TYPE: DNA
<213> ORGANISM: Gallus gallus

<400> SEQUENCE: 32
gaggaagatc catgcgaatg taaatctata gtgaagttcc agacaaaagt tgaagaactc      60
atcaatacac tgcaacagaa attggaagct gtggcaaaaa ggattgaagc cctggagaat     120
aagatcatc                                                             129

<210> SEQ ID NO 33
<211> LENGTH: 129
<212> TYPE: DNA
<213> ORGANISM: Artificial Sequence
<220> FEATURE:
<223> OTHER INFORMATION: Modified for E. coli expression

<400> SEQUENCE: 33
gaagaagatc cgtgcgaatg taaaagcatt gtgaaatttc agaccaaagt tgaagagctg      60
atcaataccc tgcagcagaa actggaggcg gttgccaaac gcattgaagc actggagaat     120
aaaatcatc                                                             129
```

PROPHYLACTIC VACCINE AGAINST EGG DROP SYNDROME (EDS)

TECHNICAL FIELD

The present invention relates to vaccines for preventing EDS of chickens. More specifically, the invention relates to a vaccine that includes an active ingredient recombinant protein and/or a multimer thereof in which the "knob region" in the fiber protein of EDS-causing EDS virus (EDSV) is fused to a "polypeptide having a coiled-coil forming unit". Inoculation of the fused protein and/or a multimer thereof to a chicken induces high hemagglutination inhibition (HI) antibodies, and enables preventing the onset of EDS.

BACKGROUND ART

EDS is a disease of chickens characterized primarily by low egg production and abnormal egg production in chickens infected with EDSV (NPL1, and NPL 2). EDSV is classified as a member of the group III avian adenovirus, and has hemagglutination activity. The virus is characterized by proliferation in the chicken oviduct. EDS shows only minor clinical symptoms, such as mild diarrhea, if any. The disease often occurs in 30 to 40 weeks of age, where the egg production is at its peak, and causes production of eggs with abnormal shells, or low egg production over a period of 3 to 8 weeks in an infected flock. This leads to serious economic damage. Vaccines are effective for the prevention of EDS (NPL 3), and inactivated vaccines are incorporated in a wide range of vaccination programs for layers.

An EDS inactivated vaccine prepared by inactivating the viruses amplified in an embryonated domestic duck egg, and mixing the inactivated viruses with an adjuvant is currently the mainstream. While the EDSV amplification in an embryonated domestic duck egg is desirable (NPL4, and NPL 5), the emergence of avian influenza and other infections have raised concerns that the future supply of embryonated domestic duck eggs might be difficult. There accordingly is a need for a means to supply vaccine antigens that does not depend on domestic duck eggs.

EDSV has double-stranded genomic DNA of about 33 kb (NPL6). EDSV has a single serotype, and there is hardly any difference in antigenicity between strains (NPL 7). The virus particles are constructed from various structural proteins, including the core protein, the constituent hexone of the capsid, the trimeric fibers projecting out of the capsid as fibrous spikes, and a base portion, such as a penton base, providing a base for the fibers (NPL 1, and NPL 6). The neutralizing epitope is present in the hexone (NPL 8), the fiber, and the penton base (NPL 9). The fiber, in particular, has been examined in many studies (NPL 11) because of its involvement in entry into host cells (NPL 10). The fiber protein is divided into three regions by function (NPL 12). The N-terminal side involved in the linkage to the penton base (NPL 13) is called the tail, and the region in the middle is called the shaft. It is reported that the Knob at the C terminal has hemagglutination activity, and is involved in the binding to the cell receptor (NPL 11). In human adenovirus 5, the neutralizing epitope is present in the knob, one of the three regions of the fiber protein. There is a report that conformation is important to exhibit function, and that binding activity for the receptor was observed upon expression with a part of the adjacent shaft region (NPL 14).

The shaft region constituting the shaft of the fiber protein has a repeat structure with a series of multiple β spiral structures (1 repeat) including hydrophobic regions separated by proline or glycine (NPL 12, and NPL 15), and three molecules are assembled together to form a triple β spiral structure (NPL 15, and NPL 16). The knob following the shaft also has a trimeric structure (NPL 17). Typically, a shaft repeat consists of 15 amino acids (NPL 12). In EDSV, however, most repeats consist of larger numbers of amino acids (NPL 6). In human adenovirus, it is reported that reducing the shaft length leads to weaker binding to the receptor, and reduced infectivity for culture cells (NPL 18).

Concerning EDSV, there are reports that neutralizing antibodies were induced in a chicken to which the Knob, and 34 amino acids at the C-terminal portion of the shaft region adjacent to the knob were administered as an oil vaccine after expression in *Escherichia coli* (NPL 19 and NPL 20, and PTL 1).

CITATION LIST

Patent Literature

PTL 1: WO2004/078977

Non Patent Literature

NPL 1: Adair, B. M. & Fitzgerald, S. D.: Egg Drop Syndrome. In Diseases of Poultry, 12th ed. (Saif, Y M et al. ed.), p 266-276, Blackwell Publishing, Ames. 2008

NPL 2: Shigeo Yamaguchi: Egg Drop Syndrome, Disease of Birds, 7th Edition, Edited by The Japanese Society on Poultry Diseases, p 50-53, The Japanese Society on Poultry Diseases, Tokyo, 2010

NPL 3: Baxendale, W., Lutticken, D., Hein, R. & McPherson, I.: The results of field trials conducted with an inactivated vaccine against the egg drop syndrome 76 (EDS 76). Avian Pathol., 9: 77-91, 1980

NPL 4: Fujio Nonaka, Kazuo Matsuo, Shinji Yamada: Proliferation and Pathogenicity of Egg Drop Syndrome-1976 (EDS-76) Virus in Cultured Cells and Embryonated Chicken Eggs, Japan Veterinary Medical Association Journal, 37:510-515, 1984

NPL 5: Minoru Higashihara, Shinji Takai, Atsuko Hidaka, Tsutomu Houdatsu, Masami Hiruma, Yoshikazu Watanabe, Minoru Matsumoto: Isolation of the Virus of Egg Drop Syndrome 1976 (EDS-76), Jpn. J. Vet. Sci., 45: 603-612, 1983

NPL 6: Hess, M., Blocker, H. & Brandt, P.: The complete nucleotide sequence of egg drop syndrome virus: an intermediate between mastadenoviruses and aviadenoviruses. Virology, 238: 145-156, 1997

NPL 7: Tsukamoto, K., Kuwabara, M., Kaneko, M., Mase, M. & Imai, K.: No evidence for adaptation of current egg drop syndrome 1976 viruses to chickens. Avian Dis., 48: 220-223, 2004

NPL 8: Toogood, C. I., Crompton, J. & Hay, R. T.: Antipeptide antisera define neutralizing epitopes on the adenovirus hexon. J. Gen. Virol., 73: 1429-1435, 1992

NPL 9: Gahery-Segard, H., Farace, F., Godfrin, D., Gaston, J., Lengagne, R., Tursz, T., Boulanger, P. & Guillet, J. G.: Immune response to recombinant capsid proteins of adenovirus in humans: antifiber and anti-penton base antibodies have a synergistic effect on neutralizing activity. J. Virol., 72: 2388-2397, 1998

NPL 10: Louis, N., Fender, P., Barge, A., Kitts, P. & Chroboczek, J.: Cell-binding domain of adenovirus serotype 2 fiber. J. Virol., 68: 4104-4106. 1994

NPL 11: Horwitz, M. S.: Adenovirus. In Fields Virology, 4th ed., (Knipe D M et al. ed) p 2301-2326, Lippincott Williams & Wilkins, Philadelphia. 2001

NPL 12: Green, N. M., Wrigley, N. G., Russell, W. C., Martin, S. R. & McLachlan, A. D.: Evidence for a repeating cross-beta sheet structure in the adenovirus fibre. EMBO J., 2: 1357-1365, 1983

NPL 13: Hong, S. S. & Boulanger, P.: Protein ligands of the human adenovirus type 2 outer capsid identified by biopanning of a phage-displayed peptide library on separate domains of wild-type and mutant penton capsomers. EMBO J., 14: 4714-4727, 1995

NPL 14: Henry, L. J., Xia, D., Wilke, M. E., Deisenhofer, J. & Gerard, R. D.: Characterization of the knob domain of the adenovirus type 5 fiber protein expressed in *Escherichia coli*. J. Virol., 68: 5239-5246, 1994

NPL 15: van Raaij, M. J., Mitraki, A., Lavigne, G. & Cusack, S.: A triple beta-spiral in the adenovirus fibre shaft reveals a new structural motif for a fibrous protein. Nature, 401: 935-938, 1999

NPL 16: Stouten, P. F., Sander, C., Ruigrok, R. W. & Cusack, S.: New triple-helical model for the shaft of the adenovirus fibre. J. Mol. Biol., 226: 1073-1084, 1992

NPL 17: Xia, D., Henry, L., Gerard, R. D. & Deisenhofer, J. Structure of the receptor binding domain of adenovirus type 5 fiber protein. Curr. Top Microbiol. Immunol., 199: 39-46, 1995

NPL 18: Shayakhmetov, D. M. & Lieber, A.: Dependence of adenovirus infectivity on length of the fiber shaft domain. J. Virol., 74: 10274-10286, 2000

NPL 19: Gutter, B., Fingerut, E., Gallili, G., Eliahu, D., Perelman, B., Finger, A. & Pitcovski, J.: Recombinant egg drop syndrome subunit vaccine offers an alternative to virus propagation in duck eggs. Avian Pathol., 37: 33-37, 2008

NPL 20: Fingerut, E., Gutter, B., Gallili, G., Michael, A. & Pitcovski, J.: A subunit vaccine against the adenovirus egg-drop syndrome using part of its fiber protein. Vaccine, 21: 2761-2766, 2003

NPL 21: Adv. Protein Chem. 2005, 70, 37-78

SUMMARY OF INVENTION

Technical Problem

The present invention is intended to provide a recombinant EDS vaccine capable of effectively preventing EDS, intended for farms with potential EDS risks.

Solution to Problem

In order to find a solution to the foregoing problems, the present inventors examined the structure of EDSV fiber protein using a structure prediction model, and found that the boundary between the knob region and the shaft region exists closer to the N terminal than conventionally thought. It was also found that a recombinant protein and/or a multimer thereof in which a knob region demarcated so as not to contain the shaft region was fused to a polypeptide having a coiled-coil forming unit induce high HI antibodies when inoculated as a vaccine to a chicken. The present invention was completed on the basis of these findings.

Specifically, the present invention is as follows.

A fused protein in which a polypeptide having a coiled-coil forming unit is bound to a knob region in a fiber protein of EDSV.

A fused protein in which the polypeptide having a coiled-coil forming unit is a GCN4 or a cartilage matrix protein (CMP).

A fused protein multimer of the fused protein.

A nucleic acid fragment including a DNA sequence that encodes the fused protein.

A recombinant expression vector including the nucleic acid fragment.

A transformant with the nucleic acid fragment introduced therein.

A transformant with the recombinant expression vector introduced therein.

An antibody that is bondable to the fused protein or to a multimer thereof.

A vaccine for EDS containing the fused protein as an active ingredient.

A therapeutic agent for EDS containing the antibody as an active ingredient.

A DNA vaccine for EDS containing the nucleic acid fragment or the recombinant expression vector as an active ingredient.

A kit including the fused protein or a multimer thereof, wherein the kit is for measurement of an antibody level against the knob region of EDSV in a test sample.

A kit including the antibody, wherein the kit is for measurement of the content of the knob region of EDSV in a test sample.

A method for preventing EDS, the method including administering the fused protein, a multimer thereof, the nucleic acid fragment, or the recombinant expression vector to a chicken.

A method for treating EDS, the method including administering the antibody to a chicken.

Advantageous Effects of Invention

A vaccine of the present invention including a recombinant protein and/or a multimer thereof contained as active ingredients and in which the knob region of EDSV is fused to a polypeptide having a coiled-coil forming unit induces high HI antibodies when inoculated to a chicken, and can prevent the onset of EDS in chickens.

BRIEF DESCRIPTION OF DRAWINGS

FIG. 1 is a schematic view of fused proteins prepared in Examples 1 to 4 and Comparative Example 1.

FIG. 2 is a diagram representing SDS-PAGE analysis confirming formation of multimers of the fused proteins prepared in Examples 1 to 4 and Comparative Example 1.

DESCRIPTION OF EMBODIMENTS

Figure 3:
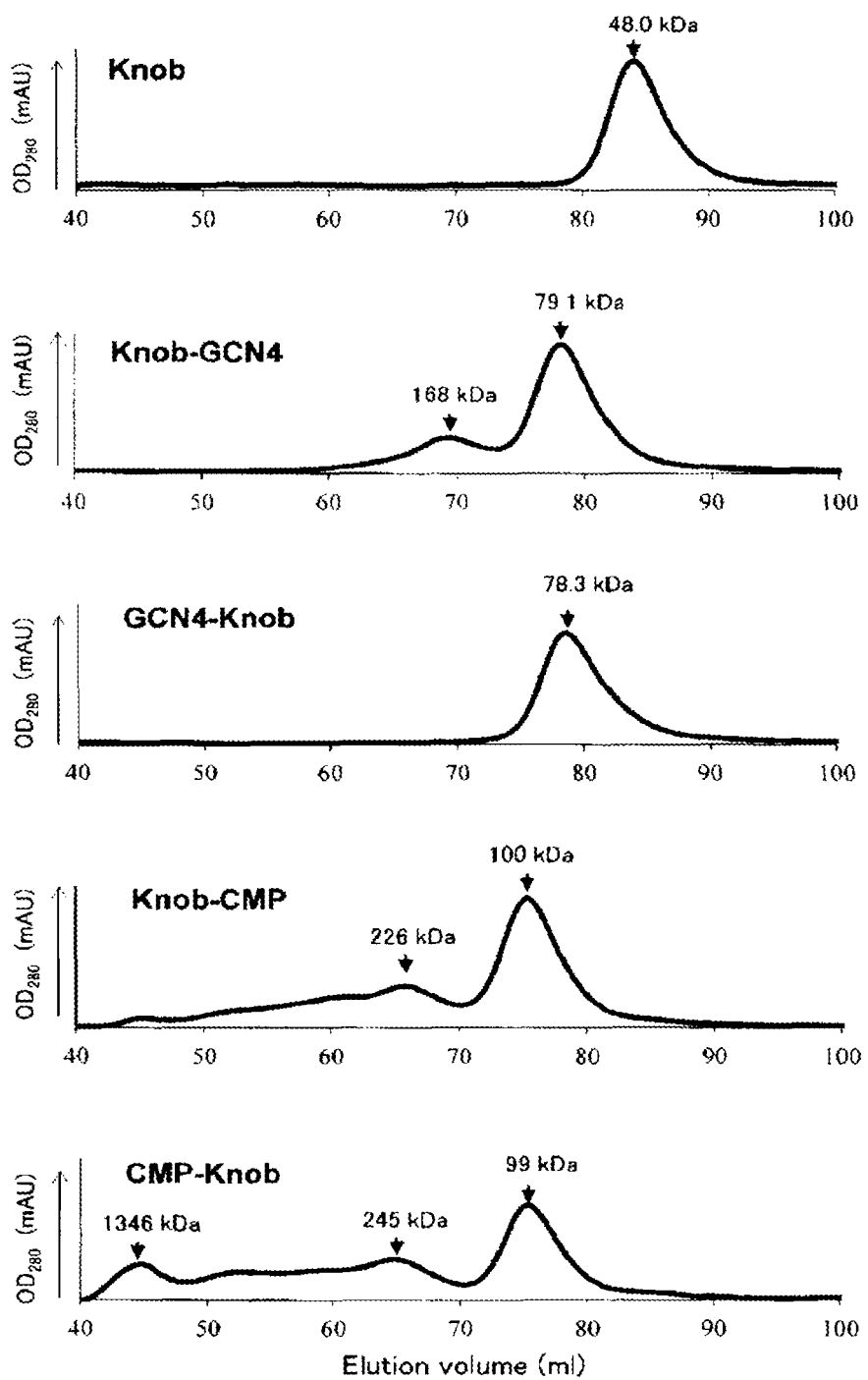
FIG. 3 is a diagram representing gel-filtration molecular weight distribution analysis of the fused proteins prepared in Examples 1 to 4 and Comparative Example 1.

The present invention includes a fused protein in which a polypeptide having a coiled-coil forming unit is bound to the knob region in the fiber protein of a chicken EDSV.

The fiber protein of EDSV is divided into three regions by function: the tail, the shaft, and the knob from the N-terminal side. Preferably, the knob region of EDSV constituting the fused protein of the present invention does not contain the shaft region because it has a risk of lowering solubility. On the other hand, it is preferable to fully contain the knob region to avoid the risk of losing the native higher-order structure of the knob region. Examples of such a knob region of EDSV include a polypeptide consisting of the amino acid sequence represented by SEQ ID NO: 11. This amino acid sequence includes a portion with nine N-terminal amino acids which were thought to be contained in the shaft region (NPL 20). However, studies by the present inventors based on a structure prediction model predicted that the knob region extends to this position. The knob region of EDSV constituting the fused protein of the present invention includes a polypeptide consisting of the amino acid sequence represented by SEQ ID NO: 11, and a polypeptide consisting of the amino acid sequence of SEQ ID NO: 11 with the deletion, substitution, or addition of one or several amino acids. As used herein, "several amino acids" means typically 2 to 9, preferably 2 to 5, further preferably 2 to 3 amino acids. The knob region also includes a polypeptide consisting of an amino acid sequence that is at least 80%, preferably at least 90%, more preferably at least 95% homologous to the foregoing amino acid sequences.

The gene that encodes the knob region of EDSV includes the DNA sequence of SEQ ID NO: 12, a DNA sequence for which the codons have been optimized for expression in *Escherichia coli* or yeast, a DNA sequence prepared by adding a suitable restriction enzyme cutting site to these DNA sequences, and a DNA sequence obtained after the deletion, substitution, or addition of one or several bases in the foregoing DNA sequences. As used herein, "several bases" means typically 2 to 9, preferably 2 to 5, further preferably 2 to 3 bases. The coding gene also includes a DNA sequence that is at least 80%, preferably at least 90%, more preferably at least 95% homologous to the foregoing DNA sequences.

The polypeptide having a coiled-coil forming unit that binds to the Knob to constitute the fused protein of the present invention is not particularly limited, as long as it has the ability to form a coiled coil structure. Preferably, the polypeptide is one having a coiled-coil forming unit derived from a protein that forms a native multimer (a multimer-forming protein). The multimer-forming proteins described in NPL 21 (Adv. Protein Chem. 2005, 70, 37-78) are examples of such proteins. Preferably, the polypeptide is one having a coiled-coil forming unit derived from, for example, GCN4, chicken-derived CMP, or bacteriophage T4-derived fibritin, more preferably GCN4, and CMP, particularly preferably CMP, because a fused protein of the Knob with such polypeptides can be obtained as a soluble protein in high yield, and has a desirable HI antibody inducing effect.

The polypeptide having a GCN4 coiled-coil forming unit includes a dimeric polypeptide consisting of the amino acid sequence of SEQ ID NO: 27, a trimeric polypeptide consisting of the amino acid sequences of SEQ ID NOS: 28 to 30, and a polypeptide consisting of an amino acid sequence obtained after the deletion, substitution, or addition of one or several amino acids in these amino acid sequences. The polypeptide having a GCN4 coiled-coil forming unit also includes a polypeptide consisting of an amino acid sequence that is at least 80%, preferably at least 90%, more preferably at least 95% homologous to the foregoing amino acid sequences. Preferred is the trimeric form, and a polypeptide consisting of the amino acid sequence of SEQ ID NO: 30 is particularly preferred.

The polypeptide having a CMP coiled-coil forming unit includes a polypeptide consisting of the amino acid sequence of SEQ ID NO: 31, and a polypeptide consisting of the amino acid sequence of SEQ ID NO: 31 with the deletion, substitution, or addition of one or several amino acids. The polypeptide having a CMP coiled-coil forming unit also includes a polypeptide consisting of an amino acid sequence that is at least 80%, preferably at least 90%, more preferably at least 95% homologous to the foregoing amino acid sequences.

The DNA sequence that encodes the polypeptide having a CMP coiled-coil forming unit includes the DNA sequence of SEQ ID NO: 32, a DNA sequence of, for example, SEQ ID NO: 33 for which the codons have been optimized for expression in *Escherichia coli*, a DNA sequence prepared by adding a suitable restriction enzyme cutting site to these DNA sequences, and a DNA sequence obtained after the deletion, substitution, or addition of one or several bases in the foregoing DNA sequences. The DNA sequence that encodes the polypeptide having a CMP coiled-coil forming unit also includes a DNA sequence that is at least 80%, preferably at least 90%, more preferably at least 95% homologous to the foregoing DNA sequences.

In the fused protein of the present invention, the polypeptide having a coiled-coil forming unit of, for example, GCN4 and CMP may be bound to either the N-terminal side or the C-terminal side of the Knob. For example, when the coiled-coil forming unit is a CMP, a HI antibody inducing effect can be obtained regardless of whether the polypeptide is bound to the N-terminal side or the C-terminal side of the Knob. On the other hand, when GCN4 is used, a higher HI antibody inducing effect is obtained when the polypeptide is bound to the N-terminal side of the Knob. The peptide having a coiled-coil forming unit, and the Knob may be bound adjacent to each other. However, a spacer, such as a linker sequence, may be inserted between the two for purposes such as reducing the intermolecular interaction between these regions. Such a linker sequence is not particularly limited, and a combination sequence of GPGP $(GP)_2$ or $GGGGS(G_4S)$ may be used, for example. It is also possible to use a sequence with one to four $(G_4S)$ repeats $((G_4S)_1$ to $(G_4S)_4)$ as the linker sequence, optionally in combination with $(GP)_2$. The sequence may be a Hisx6 $(H_6)$ tag sequence. Preferred examples of the linker sequence, or a combination of the tag sequence and the linker sequence include $(G_4S)_1$, $(G_4S)_2$, $(G_4S)_2H_6(G_4S)_2$, and $(G_4S)_2H_6(G_4S)_1(G_3S)_1$. The tag sequence may be added to the N terminal or the C terminal of the fused protein.

An example of the fused protein of the present invention is a fused protein Knob-GCN4 (for example, SEQ ID NO: 13 (amino acid sequence), SEQ ID NO: 14 (DNA sequence)) in which a polypeptide having a GCN4 coiled-coil forming unit is added to the C-terminal side of the Knob with the linker sequence $((G_4S)_2)$ inserted between the two, and the tag sequence $(H_6)$ attached to the C terminal. Another example is a fused protein GCN4-Knob (for example, SEQ ID NO: 21 (amino acid sequence), SEQ ID NO: 22 (DNA sequence)) in which a polypeptide having a GCN4 coiled-coil forming unit is disposed on the N-terminal side of the Knob with the linker sequence $((G_4S)_1)$ inserted between the two, and a tag sequence $(H_6)$ attached to the C terminal. The fused protein of the present invention includes not only a protein represented by the amino acid sequence of SEQ ID NO: 13 or 21, but a polypeptide consisting of an amino acid sequence obtained after the deletion, substitution, or addition of one or several amino acids in these amino acid sequences. The fused protein also includes a polypeptide consisting of an amino acid sequence that is at least 80%, preferably at least 90%, more preferably at least 95% homologous to the foregoing amino acid sequences.

Other examples of the fused protein of the present invention include a fused protein (for example, SEQ ID NO: 23 (amino acid sequence), SEQ ID NO: 24 (DNA sequence)) in which a polypeptide having a CMP coiled-coil forming unit is bound to the C-terminal side of the Knob with a tag sequence (Hd and a linker sequence $((G_4S)_2)$ inserted between the two, and a fused protein (for example, SEQ ID NO: 25 (amino acid sequence), SEQ ID NO: 26 (DNA sequence)) in which a polypeptide having a CMP coiled-coil forming unit is bound to the N terminal of the Knob with a tag sequence and linker sequence combination $((G_4S)_2H_6(G_4S)_1(G_3S)_1)$ inserted between the two. The fused protein of the present invention includes not only a protein represented by the amino acid sequence of SEQ ID NO: 23 or 25, but a polypeptide consisting of an amino acid sequence obtained after the deletion, substitution, or addition of one or several amino acids in these amino acid sequences. The fused protein of the present invention also includes a polypeptide consisting of an amino acid sequence that is at least 80°, preferably at least 90°, more preferably at least 95° homologous to the foregoing amino acid sequences.

For the binding of the polypeptide having a coiled-coil forming unit and the Knob, these may be expressed after being bound to each other by genetic engineering. In an exemplary method, an expression vector is created that places the DNA sequence of the coiled-coil forming unit and the DNA sequence of the Knob adjacent to each other, and the expression vector is introduced into a suitable host to express the fused protein. The DNA sequence of the coiled-coil forming unit may be disposed at the 5' end or the 3' end of the DNA sequence of the Knob. When creating the expression vector, the DNA sequences of a linker sequence and/or a tag sequence may be inserted between the DNA sequence of the coiled-coil forming unit and the DNA sequence of the Knob, or may be added to the 5' end or the 3' end of the DNA sequence. In an exemplary method, an expression vector may be created in which the DNA sequence of the Knob, the DNA sequences of the tag sequence and/or the linker sequence, and the DNA sequence of the coiled-coil forming unit are disposed from the 5' end.

The DNA sequences may be obtained by chemical synthesis, and may be used as templates for amplification by a known gene amplification technique. The DNA sequences can then be incorporated into an expression vector using various restriction enzymes to create a recombinant expression vector. Preferably, the oligonucleotide used for gene amplification is designed so that it hybridizes at the 5' end or the 3' end of the template DNA sequence, and that cutting sites for restriction enzymes are added. The template DNA may be amplified by a known gene amplification technique, using, for example, the oligonucleotide, the template DNA, and a DNA polymerase. After treating the amplified DNA sequence and the expression vector with restriction enzymes, these may be ligated to each other with a suitable DNA ligase to construct a recombinant expression vector in which the target DNA sequence is inserted. The present invention also includes such a recombinant expression vector.

Examples of the expression vector include plasmid vectors, phage vectors, virus vectors, and artificial chromosome vectors. Preferred for ease of handling and cost are plasmid vectors. For example, when the host is *Escherichia coli*, the expression vector may be, for example, a pFN6A (HQ) Flexi Vector (Promega), a pFN7A (HQ) Flexi Vector (Promega), a pFN2A (GST) Flexi Vector (Promega), apET-15b (MERCK), apET-21d (MERCK), apUC57 (GenScript), apET-22b (MERCK), a pET-21d (MERCK), or a pCold vector (Takara Bio). In the case of mammals, the expression vector may be, for example, a pF4A CMV Flexi Vector (Promega), a pF5A CMV-neo Flexi Vector (Promega), a pF9A CMV hRluc-neo Flexi Vector (Promega), or a pCI-neo Mammalian Expression Vector (Promega). The expression vector may include a replication origin, a promoter sequence having a regulatory role for gene expression, a regulatory sequence such as an enhancer sequence, and a selection marker sequence.

Examples of the promoter sequence include bacteria promoters, including the *E. coli* lacI and lacZ promoters, the T3 and T7 promoters, the gpt promoter, the lambda PR and PL promoters, the tac promoter, and the trp and trc promoters. With regard to the promoter sequence, examples of known suitable eukaryotic cell promoters include the cytomegalovirus (CMV) immediate promoter, the herpes simplex virus (HSV) thymidine kinase promoter, the early and late simian virus (SV) 40 promoter, and the retrovirus long terminal repeat (LTR) promoter, including, for example, the Rous sarcoma virus (RoSV) promoter, and metallothionein promoters such as the metallothionein-I promoter.

For expression of the fused protein using higher eukaryotic cells as a host, an enhancer sequence may be inserted into the expression vector to enhance transcription activity. The enhancer sequence acts to enhance the transcription activity of the promoter in a predetermined host cell type. Examples of the enhancer include the SV40 enhancer, the CMV early promoter enhancer, the polyoma enhancer on the late side of the replication origin, the β actin enhancer, and the adenovirus enhancer.

Examples of the selection marker include the ampicillin resistant gene of *Escherichia coli*, the trp1 gene of *Saccharomyces Cerevisiae*, and the neomycin-resistant gene of mammalian cells.

The present invention includes a nucleic acid fragment that contains the DNA sequence of the coiled-coil forming unit, and the DNA sequence of the Knob, and that encodes the fused protein of the present invention. The nucleic acid fragment of the present invention includes a nucleic acid fragment in which the DNA sequence of the coiled-coil forming unit and the DNA sequence of the Knob are contiguously disposed, and a nucleic acid fragment in which the DNA sequence of a tag sequence and/or a linker sequence is inserted between the DNA sequence of the coiled-coil forming unit and the DNA sequence of the Knob. For example, the nucleic acid fragment includes the nucleic acid fragment of SEQ ID NO: 14, 24, 26, or 28.

The full sequence of the nucleic acid fragment of the present invention may be obtained by chemical synthesis. The nucleic acid fragment of the present invention may also be obtained by joining a part of the nucleic acid fragment and the rest of the nucleic acid fragment by using a known gene recombination technique after obtaining these partial nucleic acid fragments by chemical synthesis. For example, after the chemical synthesis of the DNA sequence of the Knob or the coiled-coil forming unit, these are amplified by using a known gene amplification technique, and inserted into separate cloning vectors. The DNA sequence of the Knob or the DNA sequence of the coiled-coil forming unit is then cut from the cloning vector with restriction enzyme, and inserted into an expression vector that has been treated with restriction enzyme in the same fashion to create a recombinant expression vector. The vector is designed so that these fragments are contiguously disposed upon being inserted. The recombinant expression vector can then be cut with restriction enzyme or the like to obtain a nucleic acid fragment containing the joined DNA sequence of the coiled-coil forming unit and the Knob. For the production of the nucleic acid fragment using this method, the DNA sequence of a tag sequence or a linker sequence may be inserted between the DNA sequences of the coiled-coil forming unit and the Knob to create an expression vector, and obtain the nucleic acid fragment.

The expression vector created in the manner described above may be used to transform a host, and obtain a transformant containing the expression vector. The present invention includes such transformants. The host may be a known host, for example, such as *Escherichia coli*, yeasts, mammalian cell lines, insect cells, and plants. Examples of *Escherichia coli* include the BL21 strain, and DH5α. Examples of the yeasts include *Pichia pastoris*, and *Saccharomyces cerevisiae*. Examples of mammalian cells include the CHO cells, the HEK293 cells, and the COS-1/-7 cells.

The expression vector may be introduced into the host using a known method, as may be selected according to the host. Examples of such methods include the calcium phosphate method, electroporation, and lipofection. After transfection, the host may be cultured in a medium containing a selection marker to select a transformant that has incorporated the expression vector in the host cell.

After proliferating the transformant under suitable conditions, a selected promoter may be induced under specific conditions (pH, temperature, addition of compounds) to produce the fused protein. The expressed fused protein accumulates in the cells, or is secreted from the cells.

For expression using an *Escherichia coli* host, the fused protein may be expressed into an inclusion body fraction. The inclusion body may be collected from the *Escherichia coli* by using a method, for example, such as ultrasonic disruption, high-pressure homogenization, and a method using a BugBuster (Merck).

The fused protein of the present invention obtained in the manner described above may be used as a monomer. It is, however, more preferable to use the fused protein of the present invention as a multimer because it enables inducing high HI antibodies. Such multimers of the fused protein are, for example, dimers, trimers, and higher-order multimers, and include a mixture of such multimers. For example, the fused protein is obtained as a multimer when the fused protein is expressed by using, for example, GCN4 or CMP as the polypeptide having a coiled-coil forming unit. However, the multimer may be subjected to a known refolding process, as required.

The fused protein of the present invention is a protein in which the polypeptide having a coiled-coil forming unit is bound to the Knob. These may be chemically bound to each other. As an example of such a method, the polypeptide having a coiled-coil forming unit, and the Knob may be bound to each other using a crosslinker after being separately expressed.

When separately expressing the polypeptide having a coiled-coil forming unit, and the Knob, the DNA sequences of these regions may be obtained by chemical synthesis, and the sequences may be amplified by using a known gene amplification technique using the DNA as a template to construct each expression plasmid in the manner described above. The expression plasmids may then be introduced into a host to obtain the protein of interest, as described above.

For binding using a crosslinker, it is possible to use, for example, the amino group or the thiol group (SH group) present in the protein, or the aldehyde group of the sugar chain present in the protein. However, the functional groups used are not particularly limited. For example, a method may be used in which the SH group of the polypeptide having a coiled-coil forming unit is reacted with the amino group of the Knob. Specifically, the polypeptide and the Knob may be bound to each other by being incubated after the polypeptide is subjected to a reducing process with a reducing agent such as dithiothreitol (DTT), and after introducing a pyridyldisulfide group to the Knob with N-succinyl-3-(2-pyridyldithio) proprionate (SPDP). It is also possible to chemically bind the polypeptide and the knobby taking advantage of the bonding based on interaction between biomolecules such as biotin and avidin.

The fused protein and a multimer thereof obtained in the manner described above may be isolated and purified using a common purification means. Examples of such purification means include various purification techniques, including affinity chromatography, ion-exchange chromatography, hydrophobic interaction chromatography, and gel filtration chromatography.

The present invention includes a vaccine for EDS in which the fused protein of the present invention, and/or a multimer of the fused protein are contained as active ingredients. Preferably, the vaccine of the present invention contains a multimer of the fused protein. Preferably, the multimer is a dimer, a trimer, or a higher-order multimer, or a mixture of such multimers.

Preferably, the vaccine for EDS contains the fused protein, and/or a multimer of the fused protein in an amount of 0.3 to 10 μg per dose.

The vaccine of the present invention may contain a pharmaceutically acceptable carrier. Examples of such carriers include brine, buffered brine, dextrose, water, glycerol, isotonic aqueous buffer, and combinations of these. These may be appropriately mixed with additives, for example, such as adjuvants, emulsifiers, preservatives, tonicity agents, and pH adjusters.

Examples of the adjuvants include oil adjuvants, tocopherol acetate, alum, saponins (QS21, ISCOM), and CpG oligo.

The vaccine of the present invention may be mixed with an antigen for preventing chicken infection, in addition to containing the fused protein. Examples of such infections include Newcastle disease, chicken infectious bronchitis, infectious coryza, chicken infectious bursal disease, reovirus infection, *mycoplasma* infection, and *salmonella* infection.

The vaccine of the present invention may be administered through any administration route, including transdermal administration, sublingual administration, ophthalmic administration, intracutaneous administration, intramuscular administration, oral administration, enteral administration, transnasal administration, intravenous administration, subcutaneous administration, intraperitoneal administration, and mouth-to-lung inhalation.

Concerning a relation between antibody titer and protection in conventional vaccines for EDS, protection is considered possible when the hemagglutination inhibiting antibody titer (HI antibody titer) is at least 16 fold. However, it was confirmed that the vaccine of the present invention can greatly improve the HI antibody titer over this value when administered to a chicken, and effectively prevent the occurrence of EDS.

The present invention includes a kit including the fused protein and/or a multimer of the fused protein, and for measuring an antibody level against the knob region of EDSV in a test sample. The kit including the fused protein of the present invention may be a plate with the fused protein immobilized thereon. A test sample is applied to the plate, and the fused protein on the plate is reacted with the antibodies contained in the test sample. Secondary antibodies labeled with an enzyme or a fluorescent substance are applied, and reacted with the primary antibodies. An enzyme substrate may be added, as required, and the product of the enzyme reaction or the fluorescence quantity may be detected to measure how much antibody is contained in the test sample. The kit of the present invention may be used to evaluate the efficacy of a vaccine by immunizing a chicken with a vaccine containing the fused protein and/or a multimer of the fused protein as active ingredients, and detecting the presence or absence of antibodies derived from the vaccine.

The present invention includes a DNA vaccine for EDS including the nucleic acid fragment or the recombinant expression vector as an active ingredient as mentioned above. In the DNA vaccine of the present invention, the nucleic acid fragment or the recombinant expression vector preferably includes a promoter sequence for expressing the fused protein after immunization of a chicken.

After a challenge test of a chicken conducted with EDSV be fore and after the inoculation of the DNA vaccine of the present invention to the chicken, the nucleic acid fragment or the recombinant expression vector that has significantly reduced the symptoms associated with EDS may be screened for as an active ingredient of an EDS therapeutic agent, and the amount of active ingredient may be specified from the dose.

The DNA vaccine of the present invention may contain a pharmaceutically acceptable carrier. Examples of such carriers include brine, buffered brine, dextrose, water, glycerol, isotonic aqueous buffer, and combinations of these. These may be appropriately mixed with additives, such as adjuvants, emulsifiers, preservatives, tonicity agents, and pH adjusters.

The DNA vaccine of the present invention may be administered through any administration route, including transdermal administration, sublingual administration, ophthalmic administration, intracutaneous administration, intramuscular administration, oral administration, enteral administration, transnasal administration, intravenous administration, subcutaneous administration, intraperitoneal administration, and mouth-to-lung inhalation.

The present invention includes an antibody that binds to the fused protein, and/or to a multimer of the fused protein. Production of antibodies, including monoclonal antibodies and polyclonal antibodies, or their human counterparts becomes possible when the fused protein of the present invention, and/or a multimer of the fused protein are used as antigens according to a common immunization method (Current Protocols in Molecular Biology, Antibody Engineering: A Practical Approach, Edited by J. McCafferty et al., or Antibody Engineering, Second Edition, Edited by Carl A. K. Borrebaeck). Antibodies that bind to the fused protein and/or to a multimer thereof may also be created by using an antibody producing method based on a phage display technique (Phage Display of Peptides and Proteins: A Laboratory Manual, Edited by Brian K. Kay et al., Antibody Engineering: A Practical Approach, Edited by J. McCafferty et al., or Antibody Engineering, Second Edition, Edited by Carl A. K. Borrebaeck). The antibody of the present invention has potential use as a therapeutic agent for EDS, a kit, or a carrier for affinity chromatography, as described below.

The present invention includes a therapeutic agent for EDS containing the antibody as an active ingredient. The therapeutic agent for EDS of the present invention containing the antibody as an active ingredient may contain a pharmaceutically acceptable carrier. Examples of such carriers include brine, buffered brine, dextrose, water, glycerol, isotonic aqueous buffer, and combinations of these. These may be appropriately mixed with additives, such as adjuvants, emulsifiers, preservatives, tonicity agents, and pH adjusters.

The therapeutic agent for EDS of the present invention may be administered through any administration route, including transdermal administration, sublingual administration, ophthalmic administration, intracutaneous administration, intramuscular administration, oral administration, enteral administration, transnasal administration, intravenous administration, subcutaneous administration, intraperitoneal administration, and mouth-to-lung inhalation.

The present invention includes a kit including an antibody that binds to the fused protein, and/or to a multimer of the fused protein, and for measuring the content of the knob region of EDSV in a test sample. The kit includes a kit in which an antibody that binds to the fused protein is immobilized on, for example, a plate. The kit including the antibody of the present invention may be used to evaluate the presence or absence of EDSV infection, using the knob content as an index. For example, a test sample is applied to a plate having the antibody immobilized thereon, and enzyme- or fluorescent dye-labeled antibodies are applied. After incubation, the plate is washed, and a chromogenic substrate is added, as required. The fluorescence quantity is then measured to evaluate the Knob content in the test sample.

Examples of the plate include the Nunc immunoplate MaxiSorp (Thermo scientific), the ELISA plate (Sumitomo Bakelite Co., Ltd.), the ELISPOT (MERCK), the immunoplate (Cosmo Bio Co., Ltd.), the Elisa plate (IWAKI), and the ELISA plate (ExtraGene). The antibody may be attached to the plate by using methods commonly practiced by a skilled artisan.

Examples of the method used to label antibodies with an enzyme or a fluorescent dye include the EasyLink antibody conjugation kits (abcam), the Lightning-Link Rapid Conjugation System (Innova Biosciences Ltd), the Oyster Antibody Labeling Kit (Luminartis GmbH), the enzyme labeling kit EZ-Link (PIERCE Biotechnology), the Platinum Link Protein Labeling Kit (Kreatech Biotechnology BV), and the DyLight Antibody Labeling Kit (PIERCE Biotechnology).

The present invention includes a carrier for affinity chromatography in which an antibody against the fused protein and/or a multimer of the fused protein is attached to a carrier. The fused protein of the present invention and/or a multimer of the fused protein are expressed inside and outside of the host. When expressed inside of the host, the fused protein and/or a multimer of the fused protein are collected by disrupting the host. When expressed outside of the host, the fused protein and/or a multimer of the fused protein are collected from the culture environment. The carrier of the present invention has potential use, for example, in the collection of the fused protein and/or a multimer of the fused protein from such admixture fractions.

Examples of the carrier include the HiTrap NHS-activated HP (GE Healthcare), the NHS-activated Sepharose 4 Fast Flow (GE Healthcare), the CNBr-activated Sepharose 4B (GE Healthcare), the CNBr-activated Sepharose 4 Fast Flow (GE Healthcare), the EAH Sepharose 4B (GE Healthcare), the ECH Sepharose 4B (GE Healthcare), the Profinity epoxy resin (BIORAD), and the Affi-Gel Hz Hydrazide gel (BIO-RAD). The antibody may be attached by using methods commonly practiced by a skilled artisan.

EXAMPLES

The following describes the present invention in greater detail, referring to Examples. The present invention, however, is in no way limited by the following descriptions.

Example 1

Preparation of Knob-GCN4 Protein and Multimer Thereof
(1) Construction of Knob-GCN4 Expression Vector Genomic DNA was extracted from the EDSV KE-80 strain as follows. After inoculating the virus inside the allantoic cavity of an embryonated egg of a 9-day-old duck, the allantoic fluid collected on day 6 of inoculation was added to a pronase solution to which proteinase K (1 mg/ml) had been added. The mixture was then shaken at 50° C. for 1 h, and further shaken overnight at 37° C. This was followed by protein removal by phenol/chloroform, ethanol precipitation, and RNase A (Qiagen) treatment to extract virus genomic DNA.

By using the extracted virus genomic DNA as a template, a DNA fragment (SEQ ID NO: 6) that encodes the knob region of the fiber protein and a part of 8 repeats of the shaft region (SEQ ID NO: 5) was amplified by polymerase chain reaction (PCR), using a sense strand primer having an NcoI recognition sequence (SEQ ID NO: 3) and an antisense strand primer having an XhoI recognition sequence (SEQ ID NO: 4). The amplified DNA fragment and a plasmid pET-15b (Merck) were cut with restriction enzymes NcoI and XhoI, and ligated to each other with DNA ligase. The ligated product was then introduced into *Escherichia coli* DH5α. The resulting plasmid from the *Escherichia coli* was obtained as intermediate vector 1.

For expression in *Escherichia coli* of a polypeptide having a $(G_4S)_2$ linker sequence added to a GCN4 trivalent coiled-coil forming unit (hereinafter, "GCN4") of a modified GCN4 protein (NCBI*: 1CZQ_A) (hereinafter, the polypeptide will be referred to as "$(G_4S)_2$-GCN4"; SEQ ID NO: 7), the codons of the DNA sequence encoding the $(G_4S)_2$-GCN4 was optimized, and a DNA sequence (SEQ ID NO: 8) was artificially synthesized that was designed to include a 5' NcoI recognition sequence and a 3' XhoI recognition sequence for cloning into an expression vector. The synthesized DNA and a plasmid pET-21d (Merck) were cut with restriction enzymes NcoI and XhoI, and ligated to each other with DNA ligase. The ligated product was then introduced into *Escherichia coli* DH5α. The resulting plasmid from the *Escherichia coli* was obtained as intermediate vector 2.

By using the intermediate vector 1 as a template, a DNA fragment (SEQ ID NO: 12) that encodes the Knob (SEQ ID NO: 11) was amplified by PCR using a sense strand primer having an NcoI recognition sequence (SEQ ID NO: 9) and an antisense strand primer having an NcoI recognition sequence (SEQ ID NO: 10). The amplified DNA fragment and the intermediate vector 2 were cut with restriction enzyme NcoI, and ligated to each other with DNA ligase. The ligated product was then introduced into *Escherichia coli* DH5α. The resulting plasmid from the *Escherichia coil* was obtained as pKNOB2. The pKNOB2 includes a DNA sequence (SEQ ID NO: 14) that encodes a polypeptide (hereinafter, "Knob-GCN4"; SEQ ID NO: 13; FIG. 1) composed of the knob, the $(G_4S)_2$ linker sequence, the GCN4, and Hisx6 ($H_6$) tag sequence. The pKNOB2 was introduced into *Escherichia coli* BL21 (DE3) (Merck) to obtain a Knob-GCN4-expressing *E. coli* KNOB2 strain.

(2) Culture of Recombinant *Escherichia coli*, and Purification of Expressed Protein 10 mL of LB medium and an ampicillin solution (final concentration of 100 μg/ml) was dispensed into a 200-mL Erlenmeyer flask, and the Knob-GCN4-expressing *E. coli* KNOB2 strain was inoculated, and shake cultured at 37° C. for about 14 h (preculture). 250 mL of LB medium and an ampicillin solution (final concentration of 100 μg/ml) was dispensed into a 2-L Erlenmeyer flask, and 5 ml of the preculture bacterial solution was inoculated, and shake cultured at 37° C. until $OD_{590}$ exceeded 0.6. Upon the $OD_{590}$ of the main culture exceeding 0.6, isopropyl-β-D-galactopyranoside (IPTG) was added to make the final concentration 1 mM, and the cells were shake cultured at 37° C. for 4 h. The main culture solution was transferred to a centrifuge tube, and centrifuged at 8,000 rpm at 4° C. for 30 min. The resulting bacteria pellet was then collected.

Two tablets of the complete protease inhibitor cocktail tablet (Roche) were added to 50 mL of BugBuster Master Mix (Novagen) to obtain a cell disrupting solution. The bacteria pellet was suspended in the cell disrupting solution, incubated at room temperature for 60 min, and ultrasonically disrupted (on ice, Output 4, Duty 70%, 10 min×3 times). The disrupted solution was centrifuged (15,000 rpm, 4° C., 30 min), and the supernatant (soluble fraction) was collected.

The recombinant antigen protein contained in the soluble fraction was purified using a HisTrap HP, 5 ml column (GE Healthcare) according to the manufacturer's protocol appended to the column. The soluble fraction was applied to the column after adding 20 mM (final concentration) of imidazole to the solution, and the column was eluted with a buffer containing 500 mM (final concentration) of imidazole after washing the column with a buffer containing 20 mM (final concentration) of imidazole. The resulting elution fraction was concentrated with Amicon Ultra-15 10K (Millipore), and the buffer component was displaced with PBS by dialysis to obtain Knob-GCN4 antigens.

Example 2

Preparation of GCN4-Knob Protein and Multimer Thereof
(1) Construction of GCN4-Knob Expression Vector By using the intermediate vector 2 as a template, a DNA fragment (SEQ ID NO: 18) that encodes a polypeptide containing GCN4 and a $(G_4S)_1$ linker sequence added thereto (hereinafter, the polypeptide will be referred to as "GCN4-$(G_4S)_1$"; SEQ ID NO: 17) was amplified by PCR, using a sense strand primer having an NcoI recognition sequence (SEQ ID NO: 15) and an antisense strand primer having an XhoI recognition sequence (SEQ ID NO: 16). The amplified DNA fragment and a plasmid pET-21d (Merck) were cut with restriction enzymes NcoI and XhoI, and ligated to each other with DNA ligase. The ligated product was then introduced into *Escherichia coli* DH5α. The resulting plasmid from the *Escherichia coli* was obtained as intermediate vector 3.

By using the intermediate vector 1 as a template, a DNA fragment (SEQ ID NO: 12) that encodes the Knob (SEQ ID NO: 11) was amplified by PCR, using a sense strand primer having an XhoI recognition sequence (SEQ ID NO: 19) and an antisense strand primer having an XhoI recognition sequence (SEQ ID NO: 20). The amplified DNA fragment and the intermediate vector 3 were cut with restriction enzyme XhoI, and ligated to each other with DNA ligase. The ligated product was introduced into *Escherichia coli* DH5α. The resulting plasmid from the *Escherichia coli* was obtained as pKNOB3. The pKNOB3 has a DNA sequence (SEQ ID NO: 22) that encodes a polypeptide composed of the GCN4, the $(G_4S)_1$ linker sequence, the Knob, and the histidine hexamer tag sequence (the polypeptide will be referred to as "GCN4-Knob"; SEQ ID NO: 21; FIG. 1). The pKNOB3 was introduced into *Escherichia coli* BL21 (DE3) (Merck) to obtain a GCN4-Knob-expressing *E. coli* KNOB3 strain.

(2) The recombinant *Escherichia coli* was cultured, and the expressed protein was purified in the same manner as in Example 1 to obtain GCN4-Knob antigens.

Example 3

Preparation of Knob-CMP Protein and Multimer Thereof
(1) Construction of Knob-CMP Expression Vector For expression in *Escherichia coli* of a polypeptide composed of the Knob, a $(G_4S)_2H_6(G_4S)_2$ linker sequence, and a trivalent coiled-coil forming unit of a CMP protein (NCBI#: NP_001025546) (hereinafter, the polypeptide will be referred to as "Knob-CMP"; SEQ ID NO: 23; FIG. 1), the codons of the DNA sequence encoding the polypeptide was optimized, and a DNA sequence (SEQ ID NO: 24) was artificially synthesized that was designed to include a 5' NdeI recognition sequence, a 3' BamHI recognition sequence, and 5' and 3' protecting bases for cloning into an expression vector. The synthesized DNA, and a plasmid pUC57 (GenScript Inc.) cut with restriction enzyme EcoRV were ligated to each other with DNA ligase. The ligated product was then introduced into *Escherichia coli* DH5α. The resulting plasmid from the *Escherichia coli* was obtained as intermediate vector 4.

The intermediate vector 4 was cut with restriction enzymes NdeI and BamHI to obtain a DNA fragment that encodes Knob-CMP. The DNA fragment, and a plasmid pET-11a (Merck) cut with restriction enzymes NdeI and BamHI were ligated to each other with DNA ligase. The ligated product was introduced into *Escherichia coli* DH5α. The resulting plasmid from the *Escherichia coli* was obtained as pKNOB4. The pKNOB4 was then introduced into *Escherichia coli* BL21 (DE3) (Merck) to obtain a Knob-CMP-expressing *E. coli* KNOB4 strain.

(2) The recombinant *Escherichia coli* was cultured, and the expressed protein was purified in the same manner as in Example 1 to obtain Knob-CMP antigens.

Example 4

Preparation of CMP-Knob Protein and Multimer Thereof
(1) Construction of CMP-Knob9 Expression Vector For expression in *Escherichia coli* of a polypeptide composed of a CMP, a $(G_4S)_2H_6(G_4S)_1(G_3S)_1$ linker sequence, and the Knob (hereinafter, the polypeptide will be referred to as "CMP-Knob"; SEQ ID NO: 25; FIG. 1), the codons of the DNA sequence encoding the polypeptide was optimized, and a DNA sequence (SEQ ID NO: 26) was artificially synthesized that was designed to include a 5' NdeI recognition sequence, a 3' BamHI recognition sequence, and 5' and 3' protecting bases for cloning into an expression vector. The synthesized DNA, and a plasmid pUC57 (GenScript Inc.) cut with restriction enzyme EcoRV were ligated to each other with DNA ligase. The ligated product was then introduced into *Escherichia coli* DH5α. The resulting plasmid from the *Escherichia coli* was obtained as intermediate vector 5.

The intermediate vector 5 was cut with restriction enzymes NdeI and BamHI to obtain a DNA fragment that encodes CMP-Knob. The DNA fragment, and a plasmid pET-11a (Merck) cut with restriction enzymes NdeI and BamHI were ligated to each other with DNA ligase. The ligated product was introduced into *Escherichia coli* DH5α. The resulting plasmid from the *Escherichia coli* was obtained as pKNOB5. The pKNOB5 was then introduced into *Escherichia coli* BL21 (DE3) (Merck) to obtain a CMP-Knob-expressing *E. coli* KNOB5 strain.

(2) The recombinant *Escherichia coli* was cultured, and the expressed protein was purified in the same manner as in Example 1 to obtain CMP-Knob antigens.

Comparative Example 1

Preparation of Knob Protein and Multimer Thereof
(1) Construction of Knob Expression Vector For expression in *Escherichia coli* of a polypeptide (SEQ ID NO: 1; FIG. 1) prepared by adding a histidine hexamer tag sequence to the knob region of the EDSV fiber protein, the codons of the DNA sequence encoding the polypeptide was optimized, and a DNA sequence (SEQ ID NO: 2) was artificially synthesized that was designed to include a 5' NdeI recognition sequence and a 3' BamHI recognition sequence for cloning into an expression vector. The synthesized DNA and a plasmid pET-11a (Merck) were cut with restriction enzymes NdeI and BamHI, and ligated to each other with DNA ligase. The ligated product was introduced into *Escherichia coli* DH5α. The resulting plasmid from the *Escherichia coli* was obtained as pKNOB1. The pKNOB1 was then introduced into *Escherichia coli* BL21 (DE3) (Merck) to obtain a Knob-expressing *E. coli* KNOB1 strain.

(2) The recombinant *Escherichia coli* was cultured, and the expressed protein was purified in the same manner as in Example 1 to obtain Knob antigens.

Test Example 1

The five recombinant antigen proteins (Knob, GCN4-Knob, Knob-GCN4, CMP-Knob, and Knob-CMP) purified in Examples 1 to 4, and Comparative Example 1 were quantified with a BCA Protein Assay Kit (Pierce). The results are presented in Table 1.

TABLE 1

| Antigen protein | Amount collected per liter of *E. coli* culture |
|---|---|
| Knob | 77 mg |
| Knob-GCN4 | 21 mg |
| GCN4-Knob | 37 mg |
| Knob-CMP | 15 mg |
| CMP-Knob | 44 mg |

Test Example 2

Analysis of Recombinant Protein Properties

The five recombinant antigen proteins (Knob, GCN4-Knob, Knob-GCN4, CMP-Knob, and Knob-CMP) purified in Examples 1 to 4 and Comparative Example 1 were analyzed by SDS-PAGE. The recombinant antigen proteins were each mixed with a sample buffer containing no reducing agent, and protein samples subjected to a heat denature treatment at 100° C. for 5 min, and protein samples without a heat denature treatment were applied to corresponding lanes on a 12.5% uniform concentration tris-glycine gel (Atto, E-R12.5L) in 2 µg/lane, and electrophorased at 10 mA for 130 min. CBB staining was performed with Ez Stain Aqua (Atto, AE-1340). For western blotting, the sample proteins were transferred to a PVDF membrane using an ordinary method. A primary antibody reaction was performed with a 1:100 dilution of anti-Knob protein chicken serum. A secondary antibody reaction was performed with a 1:4,000 dilution of anti-chicken IgG, HRP-conjugated antibody (Chicken IgG (IgY)-heavy and light chain Antibody, Bethyl Laboratories). The secondary antibody reaction was followed by a chemiluminescence reaction using a Western Lightning Plus-ECL (Perkin Elmer Life and Analytical Science), and the luminescent image produced was recorded with an Image Quant LAS4000 mini (GE Healthcare). It was confirmed that the five recombinant antigen proteins all formed molecules that were believed to be trimers (FIG. 2).

Gel filtration analysis was performed with a HiLoad 16/60 Superdex 200 prepgrade column (GE Healthcare) joined to AKTA Prime Plus (GE Healthcare). The flow rate was set to 0.8 ml/min, and PBS buffer was used. Gel Filtration Calibration Kits LMW and HMW (GE Healthcare) were used as molecular weight markers. The analysis confirmed that the five recombinant antigen proteins all formed molecules that were believed to be trimers (FIG. 3).

Test Example 3

Immunogenicity Evaluation of Recombinant Antigen (Hemagglutination Inhibition Test (HI Test))

Figure 4:
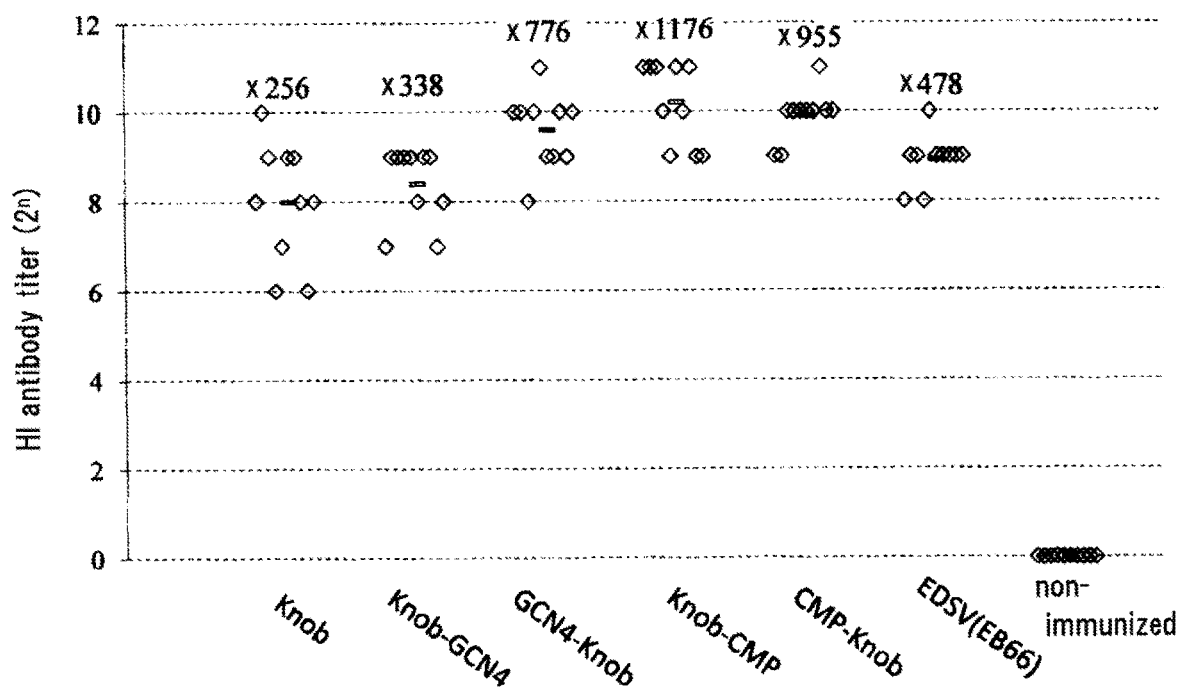
FIG. 4 is a diagram representing the results of the HI tests of chicken sera immunized with the fused proteins prepared in Examples 1 to 4 and Comparative Example 1 in Test Example 3.

The five recombinant antigen proteins (Knob, GCN4-Knob, Knob-GCN4, CMP-Knob, and Knob-CMP) purified in Examples 1 to 4 and Comparative Example 1 were used to immunize chickens, and the induced HI antibody titers were measured. Vaccines were prepared by mixing the recombinant antigen proteins with an oil adjuvant (a mixture of light liquid paraffin, sorbitan monooleate, and polysorbate 80) in an amount of 10 µg/0.5 mL in terms of the Knob. The commercially available EDS vaccine antigen EDSV (EB66) from The Chemo-Sero-Therapeutic Research Institute was used as a control vaccine. EDSV cultured with EB66 cells was mixed with an oil adjuvant (a mixture of light liquid paraffin, sorbitan monooleate, and polysorbate 80) in $10^{6.7}$ $TCID_{50}$/0.5 mL or more to prepare a vaccine. The vaccines were given to SPF chickens, 29 days of age, by intramuscularly injecting 0.5 mL of the vaccines to the leg muscle of the chickens. After 7 weeks from immunization, blood was collected from the chicken, and the collected serum was subjected to HI test. In the HI test, the test serum was mixed with 25% kaolin used in 3 times the volume of the serum (=4×dilution), and the mixture was processed for 20 min at room temperature while being shaken every 5 min. The specimen obtained after the centrifugation performed at 2,000 rpm for 5 min was used as a measurement sample. The measurement sample was serially diluted two times with PBS(−), and 0.025 mL of HA antigens prepared in 4 units/0.025 mL was added to 0.025 mL of the diluted sample. The sample was sensitized at room temperature for 10 to 20 min. Thereafter, 0.05 mL of 0.5% chicken red blood cells suspended in PBS was added, and the mixture was allowed to react at room temperature for 1 h. The HI antibody titer was then determined from the hemagglutination image. The test confirmed that the induced HI antibody titer was higher in the recombinant antigen proteins with the multimer forming unit, particularly the 3 types of recombinant antigen proteins such as the GCN4-Knob, the CMP-Knob, and the Knob-CMP (FIG. 4).

Test Example 4

Test for Confirmation of Effective Antigen Level

Figure 5:
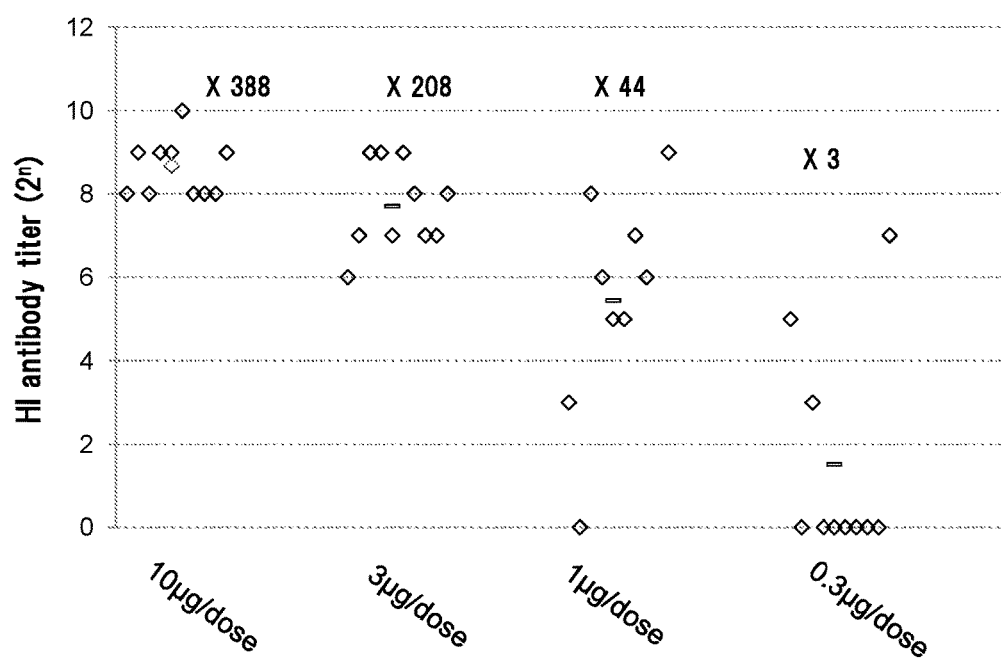
FIG. 5 is a diagram representing the results of testing for confirmation of effective antigen levels of Knob-GCN4 in Test Example 4.
Figure 6:
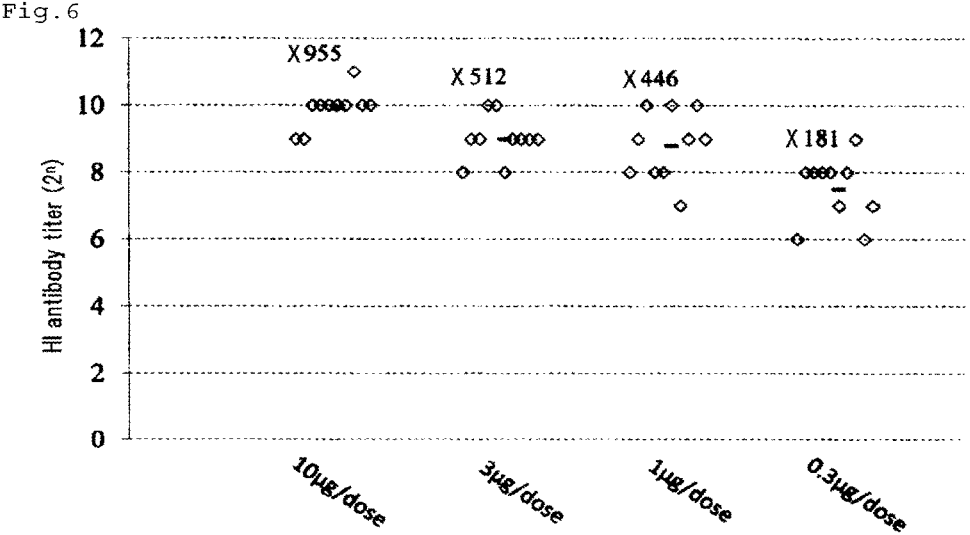
FIG. 6 is a diagram representing the results of testing for confirmation of effective antigen levels of CMP-Knob in Test Example 4.

The recombinant antigen proteins (Knob-GCN4 and CMP-Knob) purified in Examples 1 and 4 were tested to confirm effective antigen levels for chicken. Vaccines were prepared by mixing the recombinant antigen proteins (Knob-GCN4 and CMP-Knob) with an oil adjuvant (a mixture of light liquid paraffin, sorbitanmonooleate, and polysorbate 80) in amounts of 10 µg/0.5 mL, 3 µg/0.5 mL, 1 µg/0.5 mL, and 0.3 µg/0.5 mL in terms of the Knob, and were given to SPF chickens, 29 days of age, by intramuscularly injecting 0.5 mL of the vaccines to the leg muscle of the chickens. After 7 weeks from immunization, blood was collected from the chicken, and the collected serum was subjected to HI test. In the HI test, the test serum was mixed with 25% kaolin used in 3 times the volume of the serum (=4×dilution), and the mixture was processed for 20 min at room temperature while being shaken every 5 min. The specimen obtained after the centrifugation performed at 2,000 rpm for 5 min was used as a measurement sample. The measurement sample was serially diluted two times with PBS(−), and 0.025 mL of HA antigens prepared in 4 units/0.025 mL was added to 0.025 mL of the diluted sample. The sample was sensitized at room temperature for 10 to 20 min. Thereafter, 0.05 mL of 0.5% chicken red blood cells suspended in PBS was added, and the mixture was allowed to react at room temperature for 1 h. The HI antibody titer was then determined from the hemagglutination image. The test confirmed that the recombinant antigen proteins Knob-GCN4 and CMP-Knob show a desirable HI antibody inducing effect when used in 1 µg/0.5 mL or more, and 0.3 µg/0.5 mL or more, respectively (FIGS. 5 and 6).

Test Example 5

Test for Confirmation of Protective Effect Against Lethal EDSV Infection

Figure 7:
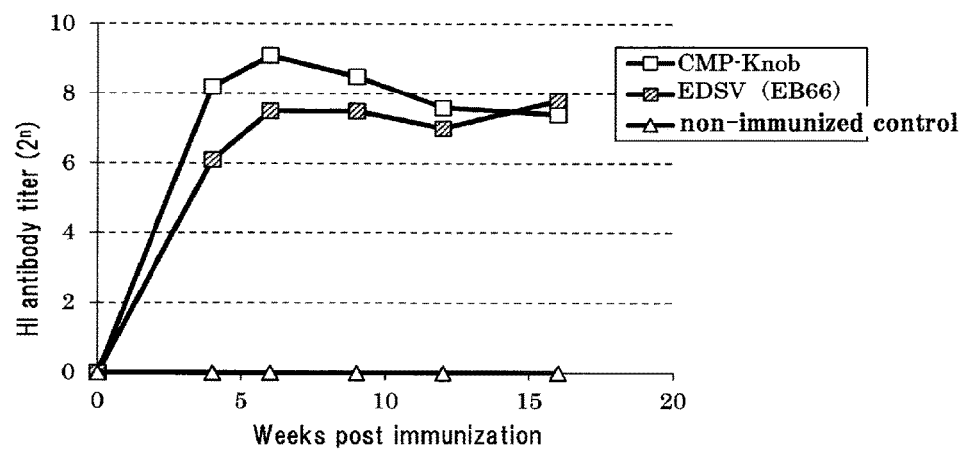
FIG. 7 is a diagram representing changes in post-immunization anti-EDSV HI antibody titers (mean values) in Test Example 5.
Figure 8:
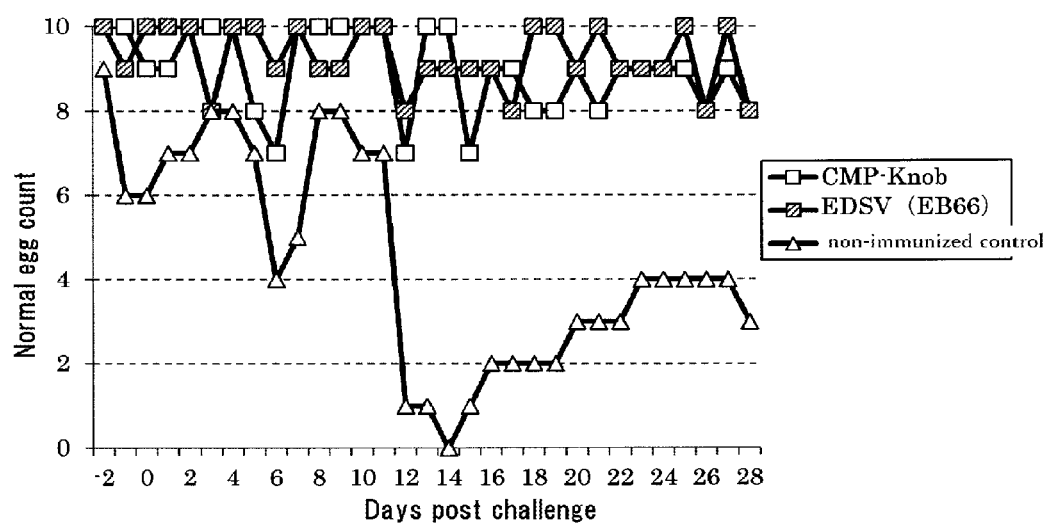
FIG. 8 is a diagram representing changes in normal egg count after lethal EDSV infection in Test Example 5.

The recombinant antigen protein (CMP-Knob) purified in Example 4 was tested to confirm its effect to protect against the onset of lethal EDSV infection in chickens immunized with the protein. A vaccine was prepared by mixing the recombinant antigen protein (CMP-Knob) with an oil adjuvant (a mixture of light liquid paraffin, sorbitan monooleate, and polysorbate 80) in an amount of 10 µg/0.5 mL in terms of the Knob. The commercially available EDS vaccine antigen EDSV (EB66) from The Chemo-Sero-Therapeutic Research Institute was used as a control vaccine. EDSV cultured with EB66 cells was mixed with an oil adjuvant (a mixture of light liquid paraffin, sorbitan monooleate, and polysorbate 80) in $10^{6.7}$ $TCID_{50}$/0.5 mL or more to prepare a vaccine. The vaccines were given to commercially available chickens (layers), about 210 days of age, by intramuscularly injecting 0.5 mL of the vaccines to the leg of the chickens. Blood was collected in week 4, 6, 9, 12, and 16 post immunization, and the collected serum was subjected to HI test. In the HI test, the test serum was mixed with 25% kaolin used in 3 times the volume of the serum (=4× dilution), and the mixture was processed for 20 min at room temperature while being shaken every 5 min. The specimen obtained after the centrifugation performed at 2,000 rpm for 5 min was used as a measurement sample. The measurement sample was serially diluted two times with PBS(−), and 0.025 mL of HA antigens prepared in 4 units/0.025 mL was added to 0.025 mL of the diluted sample. The sample was sensitized at room temperature for 10 to 20 min. Thereafter, 0.05 mL of 0.5% chicken red blood cells suspended in PBS was added, and the mixture was allowed to react at room temperature for 1 h. The HI antibody titer was then determined from the hemagglutination image. After 16 weeks from immunization, the chickens were infected by orally administering a lethal EDSV KE-80 strain in $10^{6.5}$ TCID$_{50}$/chicken. The chickens were observed for egg production for 4 weeks after the challenge. The test confirmed that the recombinant antigen protein (CMP-Knob) maintains high HI antibody titers for 16 weeks after immunization when used in 10 μg/0.5 mL (FIG. 7). It was also confirmed that clinical symptoms, such as loss of egg production, and abnormal egg production can be greatly reduced in chickens immunized with the recombinant antigen protein (CMP-Knob), even when the chickens were injected with lethal EDSV after 16 weeks from immunization (FIG. 8).

INDUSTRIAL APPLICABILITY

The vaccine of the present invention in which a recombinant protein and/or a multimer thereof containing the knob region of EDSV fused to a polypeptide having a coiled-coil forming unit are contained as active ingredients can induce high HI antibodies upon being inoculated to a chicken, and can prevent the onset of chicken EDS. The invention enables preventing the onset of EDS in farms with potential EDS risks. The vaccine of the present invention can be produced without relying on domestic duck eggs, and can be stably supplied.

---

The invention claimed is:

1. A fused protein in which a polypeptide having a coiled-coil forming unit is bound to a Knob region in a fiber protein of egg drop syndrome (EDS) virus EDSV), wherein said coiled-coil forming unit is derived from a native multimer-forming protein and said native multimer-forming protein is a GCN4 or a cartilage matrix protein (CMP) and wherein:

when said native multimer-forming protein is a GCN4 the Knob comprises a polypeptide consisting of an amino acid sequence represented by SEQ ID NO: 11 or a polypeptide having at least 95% homology to the amino acid sequence of SEQ ID NO:11; and when said native multimer-forming protein is a CMP the Knob comprises polypeptide consisting of an amino acid sequence represented by SEQ ID NO: 11.

2. The fused protein according to claim 1, comprising a linker sequence, a tag sequence, or both, between the polypeptide and the Knob.

3. The fused protein according to claim 1, wherein the native multimer-forming protein is a GCN4.

4. The fused protein according to claim 3, wherein the Knob comprises a polypeptide consisting of an amino acid sequence represented by SEQ ID NO: 11.

5. The fused protein according to claim 3, wherein the GCN4 is selected from the group consisting of SEQ ID NO: 13 and SEQ ID NO:21.

6. The fused protein according to claim 1, wherein the native multimer-tbrming protein is a cartilage matrix protein (CMP).

7. The fused protein according to claim 6, wherein the CMP is selected from the group consisting of SEQ ID NO: 23 and SEQ ID NO: 25.

8. The fused protein according to claim 1, wherein the GCN4 or the CMP is bound to the C-terminal side of the Knob.

9. The fused protein according to claim 8, wherein the GCN4 is bound to the C-terminal side of the Knob.

10. The fused protein according to claim 9, comprising a polypeptide consisting of an amino acid sequence represented by SEQ ID) NO: 13, or a polypeptide having at least 95% homology to the amino acid sequence of SEQ ID NO: 13.

11. The fused protein according to claim 8, wherein the CMP is bound to the C-terminal side of the Knob.

12. The fused protein according to claim 11, comprising a polypeptide consisting of an amino acid sequence represented by SEQ ID NO: 23, or a polypeptide having at least 95% homology to the amino acid sequence of SEC, ID NO: 23.

13. The fused protein according to claim 1, wherein the GCN4 or the CMP is bound to the N-terminal side of the Knob.

14. The fused protein according to claim 13, wherein the GCN4 is bound to the N-terminal side of the Knob.

15. The fused protein according to claim 14, comprising a polypeptide consisting of an amino acid sequence represented by SEQ ID NO: 21, or a polypeptide having at least 95% homology to the amino acid sequence of SEQ ID NO: 21.

16. The fused protein according to claim 13, wherein the CMP is bound to the N-terminal side of the Knob.

17. The fused protein according to claim 16, comprising a polypeptide consisting of an amino acid sequence represented by SEQ ID NO: 25, or a polypeptide baying at least 95% homology to the amino acid sequence of SEQ ID NO: 25.

18. A fused protein multimer of the fused protein of claim 1.

19. A vaccine for EDS, comprising the fused protein multimer of claim 18 as an active ingredient.

20. A method for preventing EDS, the method comprising administering the fused protein multimer of claim 18 to a chicken.

21. A nucleic acid fragment, comprising a DNA sequence that encodes the fused protein of claim 1.

22. A transformant with the nucleic acid fragment of claim 21 introduced therein.

23. A DNA vaccine for EDS, comprising the nucleic acid fragment of claim 21 as an active ingredient.

24. A method for preventing EDS, the method comprising administering the nucleic acid fragment of claim 21 to a chicken.

25. A recombinant expression vector, comprising the nucleic acid fragment of claim 21.

26. A transformant with the recombinant expression vector of claim 25 introduced therein.

27. A DNA vaccine for EDS, comprising the recombinant expression vector of claim 25 as an active ingredient.

28. A method for preventing EDS, the method comprising administering the recombinant expression vector of claim 25 to a chicken.

29. A vaccine for EDS, comprising the fused protein of claim 1 as an active ingredient.

30. A method for preventing EDS, the method comprising administering the fused protein of claim 1 to a chicken.

* * * * *